(12) United States Patent
Hjort et al.

US008426164B2

(10) Patent No.: US 8,426,164 B2
(45) Date of Patent: Apr. 23, 2013

(54) FUNGAL TRANSCRIPTIONAL ACTIVATOR USEFUL IN METHODS FOR PRODUCING POLYPEPTIDES

(75) Inventors: Carsten M. Hjort, Smorum (DK); Cees A. M. J. J. Van den Hondel, PZ Gouda (NL); Peter J. Punt, XT Houten (NL); Frank H. J. Schuren, ZK Veenendaal (NL); Tove Christensen, Lyngby (DK)

(73) Assignee: Novozymes A/S, Bagsvaerd (DK)

( * ) Notice: Subject to any disclaimer, the term of this patent is extended or adjusted under 35 U.S.C. 154(b) by 0 days.

(21) Appl. No.: 12/398,554

(22) Filed: Mar. 5, 2009

(65) Prior Publication Data

US 2009/0239260 A1    Sep. 24, 2009

Related U.S. Application Data

(60) Division of application No. 10/729,172, filed on Dec. 5, 2003, now Pat. No. 8,088,598, which is a division of application No. 09/525,305, filed on Mar. 14, 2000, now Pat. No. 6,806,062, which is a continuation-in-part of application No. 09/411,925, filed on Oct. 4, 1999, now abandoned.

(60) Provisional application No. 60/103,945, filed on Oct. 13, 1998.

(30) Foreign Application Priority Data

Oct. 5, 1998 (DK) ................................. 1998 01258

(51) Int. Cl.
 *C12P 21/02* (2006.01)
(52) U.S. Cl.
 USPC ...................... 435/69.1; 435/252.33; 530/350
(58) Field of Classification Search ........................ None
See application file for complete search history.

(56) References Cited

U.S. PATENT DOCUMENTS 5,179,003 A   1/1993   Wolf
6,007,988 A   12/1999  Choo

FOREIGN PATENT DOCUMENTS

| EP | 327797 | 8/1989 |
|---|---|---|
| EP | 0 574 347 | 12/1993 |
| JP | H02-2385 | 1/1990 |
| WO | WO 90/00192 | 1/1990 |
| WO | WO 95/35385 | 12/1995 |
| WO | WO 97/12045 | 4/1997 |
| WO | WO 97/35956 | 10/1997 |
| WO | WO 98/12300 | 3/1998 |

OTHER PUBLICATIONS

Gomi et al., GenEmbl Accession No. AB021876—(2000).
Dhawale et al., Oxford University Press, Nucleic Acids Research, vol. 21, No. 24, pp. 5537-5546 (1993).
Mattern et al., Mol. Gen. Genet, vol. 234, pp. 332-336 (1992).
Swiss-Prot database, accession No. P38114, Entian et al., "Putative 126.9 KD Transcriptional Regulatory Protein in YSW1-RIB7 intergenic region", see a.a. pp. 106-142 (101/1/94).
Swiss-Prot database, accession No. P39529, Purnelle et al., "Putative 86.7 KD Transcriptional Regulatory Protein in Nuc1-Nce1 intergenic region"; and Yeast vol. 10, pp. 1235-1249 (1994), see a.a. 45-76.
Swiss-Prot database, accession No. P28348, Burger et al., "Nitrogen Assimilation Transcription Factor NIRA"; and Mol. Cell. Biol. vol. 11, pp. 5746-5755 (1991).
Swiss-Prot database, accession No. P87000, Bibbins et al., "Transcriptional activator protein ACU-15", (1997).
Van Den Hambergh et al., Current Genetics, vol. 32, Part 1, pp. 73-81 (1997).
Van Den Hambergh et al., Trends in Biotechnology, vol. 15, Part 17, pp. 256-263, (1997).

*Primary Examiner* — Jim Ketter
(74) *Attorney, Agent, or Firm* — Michael W. Krenicky

(57) ABSTRACT

The present disclosure relates to isolated nucleic acid sequences encoding polypeptides having transcriptional activation activity and to the polypeptides. The disclosure also relates to nucleic acid constructs, vectors and host cells including the nucleic acid sequences. The invention further relates to host cells useful for the production of polypeptides in which the production or function of the transcriptional activator has been altered, as well as to methods for producing the polypeptides.

17 Claims, 8 Drawing Sheets

Figure 6

```
ICA217     ATGACCGCTT GTCATACCTG CCGCAAGCTT AAAACTCGGT
ICA218     ATGACTGCTT GCCACACCTG CCGCAAGCTT AAAACTCGGT

ICA217     GCGATCTTGA TCCACGAGGG CATGCCTGCC GCCGCTGCCT  (SEQ ID NO: 53)
ICA218     GCGATCTTGA TCCACGAGGG CATGCCTGCC GCCGCTGCCT  (SEQ ID NO: 54)
```

SEQUENCE LISTING

<160> NUMBER OF SEQ ID NOS: 54

<210> SEQ ID NO 1
<211> LENGTH: 4098
<212> TYPE: DNA
<213> ORGANISM: Aspergillus niger

```
<220> FEATURE:
<221> NAME/KEY: exon
<222> LOCATION: (977)..(1204)
<220> FEATURE:
<221> NAME/KEY: exon
<222> LOCATION: (1317)..(1718)
<220> FEATURE:
<221> NAME/KEY: exon
<222> LOCATION: (1777)..(2202)
<220> FEATURE:
<221> NAME/KEY: exon
<222> LOCATION: (2253)..(3116)

<400> SEQUENCE: 1
```

| | |
|---|---|
| ttggtgctgg aaagcccatt taagggatct tataaggtaa ttgccaatgt tcagtcgcct | 60 |
| atggtctttg tcgagagaaa ctctttctcg ttaagatcta catgatcgct tttgattttc | 120 |
| tctgggttca cgcggtactt tctccccgtc aatccccaac cgctgttgtg cctgaccatc | 180 |
| aatgtggaac ggataagggg acaagagaaa ttgaaggagc gatcataaaa agctaatttt | 240 |
| ggtttattat ttttttttct tataaaactc aaaaaagaaa acgaaaacga aaaggaaaa | 300 |
| aagaaaaggt aaaatggaaa aagaaaggcg gtcatcactt ccaataacca tcagccaaag | 360 |
| atacagacga gttactgacc ttcttatcct ggacttccgc ccgatccata tcttcatgat | 420 |
| aagcagggaa ccgaacaaat caacgccaac ttcagcggca gttcctcact aatttcccac | 480 |
| ttcccaccgg cgtcattttg gtcccaaccc cctccctgga agcagcggga tttagttacg | 540 |
| atccggttta catcggagac tcggaaaata ccatagcgca tgccaatcaa acccctccc | 600 |
| agggtgactg gccagtatca cgacccattg tttctatctt tctagaagac ctgcagggac | 660 |
| atggattggc tggccgccgt gctgccgtcc attagcgtct acccaggtc aagaacggac | 720 |
| tggacggacc cataaccaat ctaaccaaag ccaatttcgt caattcccag ctggcgagca | 780 |
| caatcccatt cccagggttg gccgccaact gttaaaaggc actatgtgtc tctccacctg | 840 |
| cccgccccc tcgatggcct gcgcgtaata actattctac tgcttttgc ctcttacttg | 900 |
| cctcattatt agtattttac tctactctcc agattgcctg ccagcaattg gtccaaagtg | 960 |

| | | |
|---|---|---|
| gactttgttt gatgac atg act cga acc gtg gac gag atc aaa tac gaa acg | | 1012 |
| Met Thr Arg Thr Val Asp Glu Ile Lys Tyr Glu Thr | | |
| 1 5 10 | | |
| cct tct tca tgg gag cac aag agc ttg gac gtt gcc gag gat ggc agg | | 1060 |
| Pro Ser Ser Trp Glu His Lys Ser Leu Asp Val Ala Glu Asp Gly Arg | | |
| 15 20 25 | | |
| cga cta gct ccc cat tcc gac act gct cgt ccg aaa ggc cgc ata cga | | 1108 |
| Arg Leu Ala Pro His Ser Asp Thr Ala Arg Pro Lys Gly Arg Ile Arg | | |
| 30 35 40 | | |
| cga tcg atg act gcc tgt cac aca tgt cgg aag ctt aaa act aga tgt | | 1156 |
| Arg Ser Met Thr Ala Cys His Thr Cys Arg Lys Leu Lys Thr Arg Cys | | |
| 45 50 55 60 | | |
| gat cta gat ccg cgc ggt cat gcg tgc cgt cgc tgt cta tct cta agg | | 1204 |
| Asp Leu Asp Pro Arg Gly His Ala Cys Arg Arg Cys Leu Ser Leu Arg | | |
| 65 70 75 | | |
| tcagaggcac tacctacctg ccagttgaag ctttgtcctt ctgaacgcga catgatacta | | 1264 |
| gtcgtggaat ataactgtcc caactttgct gacagtccac aatatcttta ga atc gat | | 1322 |
| Ile Asp | | |
| tgt aag ctg cct gaa acg acc gac cgc ttc caa gac agt gct gcg atg | | 1370 |
| Cys Lys Leu Pro Glu Thr Thr Asp Arg Phe Gln Asp Ser Ala Ala Met | | |
| 80 85 90 | | |
| tgg cca gac gcc acc tcg gca att ccc tcc atc gag gag cgc ctc acc | | 1418 |
| Trp Pro Asp Ala Thr Ser Ala Ile Pro Ser Ile Glu Glu Arg Leu Thr | | |
| 95 100 105 110 | | |

| | |
|---|---|
| tcc cta gaa aga tgc atg agg gag atg acg ggc atg atg cga cag atg<br>Ser Leu Glu Arg Cys Met Arg Glu Met Thr Gly Met Met Arg Gln Met<br>115                       120                  125 | 1466 |
| cta gat cac tcc cca ggt ttc gca aat gcc tcg gtt ccg cat ttg acc<br>Leu Asp His Ser Pro Gly Phe Ala Asn Ala Ser Val Pro His Leu Thr<br>           130                  135                  140 | 1514 |
| aaa agc atc atc acg gat gaa acc gcc tcg atg gag gga agc ccg tcg<br>Lys Ser Ile Ile Thr Asp Glu Thr Ala Ser Met Glu Gly Ser Pro Ser<br>145                       150                  155 | 1562 |
| tcc ccc ttc ctg cct aag ccc gtt cgc ctc att cag gac ctc cag tcc<br>Ser Pro Phe Leu Pro Lys Pro Val Arg Leu Ile Gln Asp Leu Gln Ser<br>    160                  165                  170 | 1610 |
| gac ttc ttc gga gaa gca gag act tcc ccc gtt gac tcc cct ctc tcc<br>Asp Phe Phe Gly Glu Ala Glu Thr Ser Pro Val Asp Ser Pro Leu Ser<br>175                     180                  185                  190 | 1658 |
| agc gat ggt aac gcc aag ggc gct atc gac tct aag cta tcc ctc aaa<br>Ser Asp Gly Asn Ala Lys Gly Ala Ile Asp Ser Lys Leu Ser Leu Lys<br>               195                  200                  205 | 1706 |
| ttg ttg caa acg tatgggtata cctgattgac aattaccaaa aagctgctaa<br>Leu Leu Gln Thr<br>            210 | 1758 |
| tccttggcgc aaatcagg ttt gtc gat cac ttt ggc gct tgc gtt tcc att<br>                                    Phe Val Asp His Phe Gly Ala Cys Val Ser Ile<br>                                                          215                  220 | 1809 |
| tac aat ctc tcc gac atc cac aac gac atg aaa gcc ccc gac tct tta<br>Tyr Asn Leu Ser Asp Ile His Asn Asp Met Lys Ala Pro Asp Ser Leu<br>               225                  230                  235 | 1857 |
| ctg tat aat act gca tgc ctt cta gct tca cgc tat gta ccg ggg ata<br>Leu Tyr Asn Thr Ala Cys Leu Leu Ala Ser Arg Tyr Val Pro Gly Ile<br>        240                  245                  250 | 1905 |
| ccg aca tct acc gtg cat gct ata tac ctt caa gtg cga cat gca gta<br>Pro Thr Ser Thr Val His Ala Ile Tyr Leu Gln Val Arg His Ala Val<br>255                     260                  265 | 1953 |
| gtc aat att ttg tgg gaa aaa cca ccc ctg aag tat gag acc ctc caa<br>Val Asn Ile Leu Trp Glu Lys Pro Pro Leu Lys Tyr Glu Thr Leu Gln<br>270                       275                  280                  285 | 2001 |
| gca ctt gca ctt ctc tgt ctc tgg cca gca acc gcc cag aaa gag cca<br>Ala Leu Ala Leu Leu Cys Leu Trp Pro Ala Thr Ala Gln Lys Glu Pro<br>               290                  295                  300 | 2049 |
| ccc atg gac agc tgg ctg ctg agt ggt atc tca att aac cat gca att<br>Pro Met Asp Ser Trp Leu Leu Ser Gly Ile Ser Ile Asn His Ala Ile<br>               305                  310                  315 | 2097 |
| atc gcg ctc gat ttc cta aac tat gcg ccc tcg gaa gtc atg gtg gac<br>Ile Ala Leu Asp Phe Leu Asn Tyr Ala Pro Ser Glu Val Met Val Asp<br>        320                  325                  330 | 2145 |
| aat gaa acg gct gcg cag ctg cgg cta tgg aat aca tat tgc ttg aca<br>Asn Glu Thr Ala Ala Gln Leu Arg Leu Trp Asn Thr Tyr Cys Leu Thr<br>335                     340                  345 | 2193 |
| cag cta cag tgggtttcat ctaagatctc ccgtccagaa gatagctaac<br>Gln Leu Gln<br>350 | 2242 |
| aagctttagt ttt gcg gtc ggg aat gcg cgt cct ttc cat atc cag caa<br>                   Phe Ala Val Gly Asn Ala Arg Pro Phe His Ile Gln Gln<br>                                     355                  360                  365 | 2291 |
| aga tac ctt gac cac tgc cca cgg ata ctg gag cac cca gca gca act<br>Arg Tyr Leu Asp His Cys Pro Arg Ile Leu Glu His Pro Ala Ala Thr<br>                   370                  375                  380 | 2339 |
| ctg gag gac gca agg gtt gta gca gaa ata cag ttg tat ttg atg aca<br>Leu Glu Asp Ala Arg Val Val Ala Glu Ile Gln Leu Tyr Leu Met Thr<br>385                     390                  395 | 2387 |

-continued

| | | |
|---|---|---|
| ttg cgg ctc cag agc aat agc agt cga atg cgg ttg gcg gac ctt gac<br>Leu Arg Leu Gln Ser Asn Ser Ser Arg Met Arg Leu Ala Asp Leu Asp<br>          400                 405                 410 | | 2435 |
| tat gag gaa ata gag cga tgg aag agg gag tgg gct cac ctt ttc tgt<br>Tyr Glu Glu Ile Glu Arg Trp Lys Arg Glu Trp Ala His Leu Phe Cys<br>415                 420                 425 | | 2483 |
| aag aag cct gtt ctt gtt tcc cgg gga cta cca ctg acg aga gca aca<br>Lys Lys Pro Val Leu Val Ser Arg Gly Leu Pro Leu Thr Arg Ala Thr<br>430                 435                 440                 445 | | 2531 |
| gct ggg gaa agt tcc aca ttg gag ctg agc ctt tgg ttc tgc cag aca<br>Ala Gly Glu Ser Ser Thr Leu Glu Leu Ser Leu Trp Phe Cys Gln Thr<br>                450                 455                 460 | | 2579 |
| ctc ctt cac cgc aca gca atg agg ctt cag ccc aga tcc gac agg ctc<br>Leu Leu His Arg Thr Ala Met Arg Leu Gln Pro Arg Ser Asp Arg Leu<br>            465                 470                 475 | | 2627 |
| gca tct gag gtt ctg caa acc tca cgt ctg ata ata tcg cgg ttc ctc<br>Ala Ser Glu Val Leu Gln Thr Ser Arg Leu Ile Ile Ser Arg Phe Leu<br>        480                 485                 490 | | 2675 |
| cag atc cgg tac tct acc gca tta agc ctt gtc gac caa gtc tat ttc<br>Gln Ile Arg Tyr Ser Thr Ala Leu Ser Leu Val Asp Gln Val Tyr Phe<br>495                 500                 505 | | 2723 |
| att gtc ggc tac gct gca ctg aat ctg tgc gat ttc aat ctt atg gac<br>Ile Val Gly Tyr Ala Ala Leu Asn Leu Cys Asp Phe Asn Leu Met Asp<br>510                 515                 520                 525 | | 2771 |
| ccg ctt atc gag caa gtg cag atg ttc ctg ctg cat ctc tcc ccg aac<br>Pro Leu Ile Glu Gln Val Gln Met Phe Leu Leu His Leu Ser Pro Asn<br>                530                 535                 540 | | 2819 |
| gaa gac cac atc gcc tac cgg ttt tcg tgc atg gtc gcc gag ttc aag<br>Glu Asp His Ile Ala Tyr Arg Phe Ser Cys Met Val Ala Glu Phe Lys<br>            545                 550                 555 | | 2867 |
| cgg cga tgt ggc agt gcg gaa tgc aat gac cca tca tcc act gtc aag<br>Arg Arg Cys Gly Ser Ala Glu Cys Asn Asp Pro Ser Ser Thr Val Lys<br>        560                 565                 570 | | 2915 |
| ggg tct ccg tta tca tcc tac ggc gac agt cgt aag atg agc atg ggg<br>Gly Ser Pro Leu Ser Ser Tyr Gly Asp Ser Arg Lys Met Ser Met Gly<br>575                 580                 585 | | 2963 |
| caa gca ccg ttc atg cca ccg ctc atg gat ggc atg atc gag ggg tac<br>Gln Ala Pro Phe Met Pro Pro Leu Met Asp Gly Met Ile Glu Gly Tyr<br>590                 595                 600                 605 | | 3011 |
| ggc ttc gag caa ctg atg cca gaa gtc atg ccg agt tcc ttt ccg gat<br>Gly Phe Glu Gln Leu Met Pro Glu Val Met Pro Ser Ser Phe Pro Asp<br>                610                 615                 620 | | 3059 |
| ggg ata ctc aac gga atg cct gtg act ggg cta gca gcg tat cgg tca<br>Gly Ile Leu Asn Gly Met Pro Val Thr Gly Leu Ala Ala Tyr Arg Ser<br>            625                 630                 635 | | 3107 |
| gcg acg ctg taagtaatcg agatcgggtt ggaaaggaca tgagtggggg<br>Ala Thr Leu<br>        640 | | 3156 |
| tggtggtggt agtagcagta acaccaggga tgataacctg cagcggtggt ttagttcctg | | 3216 |
| cccatgggct gaactaaaac cccgaaccta gcatgatgac gtgcaacgaa aggatcataa | | 3276 |
| ccaaggccaa gtaaatacta aaataaaata atataattcc acacgatcca ctaccaccac | | 3336 |
| caccaccgga tccatcaggt tgccttcctg cacaggccta tttagttaga gggcccgtgc | | 3396 |
| cacgaaacat cacgtaattg agcgcttttg cttccttgca acttaaacaa ccccatagac | | 3456 |
| actctcacat tcacatgcca aactactaac tcctactgac caccagctgc aggaagccag | | 3516 |
| ccagccacca tttcctaatc ggatatatct ccgaaacgta cgctttcctc ctttgttcgg | | 3576 |
| accgttccgt gcctccgcgg agagttgaac gagtcagaac acattctttt cgtttctatc | | 3636 |

-continued

```
gtttctttc caaggcagca gagagacgaa caagtcagtg cttgctaact aacttacccc    3696
tcagcatttt agtaaactac tatttaggaa agagtaatca ttcatcgaag acaagatgtt    3756
tatttctccg atcgaccaaa caaaaacgtt caggtagact aagtagtagt agtagtatgt    3816
ctttgacccc tttactccac tatccgttga ctgcacatag tagtaagtaa ctatctaacc    3876
agttgccgag gagaggaaag tgagtgggtg ggagccggag gatgccgccg agaattatta    3936
agtcgatcat tgctagttag ttatcttttc atgatgagga gaggaaggag agggggggacg    3996 ggattagaga aataaacttt tctctccaat taattatctg gattaattaa aacttggaga    4056
ggagggtagg ggagttgggt attggtatgt tgctgtgaat gt                       4098
```

<210> SEQ ID NO 2
<211> LENGTH: 666
<212> TYPE: PRT
<213> ORGANISM: Aspergillus niger

<400> SEQUENCE: 2

```
Met Thr Arg Thr Val Asp Glu Ile Lys Tyr Glu Thr Pro Ser Ser Trp
 1               5                  10                  15

Glu His Lys Ser Leu Asp Val Ala Glu Asp Gly Arg Arg Leu Ala Pro
            20                  25                  30

His Ser Asp Thr Ala Arg Pro Lys Gly Arg Ile Arg Arg Ser Met Thr
        35                  40                  45

Ala Cys His Thr Cys Arg Lys Leu Lys Thr Arg Cys Asp Leu Asp Pro
    50                  55                  60

Arg Gly His Ala Cys Arg Arg Cys Leu Ser Leu Arg Ile Asp Cys Lys
65                  70                  75                  80

Leu Pro Glu Thr Thr Asp Arg Phe Gln Asp Ser Ala Ala Met Trp Pro
                85                  90                  95

Asp Ala Thr Ser Ala Ile Pro Ser Ile Glu Glu Arg Leu Thr Ser Leu
            100                 105                 110

Glu Arg Cys Met Arg Glu Met Thr Gly Met Met Arg Gln Met Leu Asp
        115                 120                 125

His Ser Pro Gly Phe Ala Asn Ala Ser Val Pro His Leu Thr Lys Ser
    130                 135                 140

Ile Ile Thr Asp Glu Thr Ala Ser Met Glu Gly Ser Pro Ser Ser Pro
145                 150                 155                 160

Phe Leu Pro Lys Pro Val Arg Leu Ile Gln Asp Leu Gln Ser Asp Phe
                165                 170                 175

Phe Gly Glu Ala Glu Thr Ser Pro Val Asp Ser Pro Leu Ser Ser Asp
            180                 185                 190

Gly Asn Ala Lys Gly Ala Ile Asp Ser Lys Leu Ser Leu Lys Leu Leu
        195                 200                 205

Gln Thr Phe Val Asp His Phe Gly Ala Cys Val Ser Ile Tyr Asn Leu
    210                 215                 220

Ser Asp Ile His Asn Asp Met Lys Ala Pro Asp Ser Leu Leu Tyr Asn
225                 230                 235                 240

Thr Ala Cys Leu Leu Ala Ser Arg Tyr Val Pro Gly Ile Pro Thr Ser
                245                 250                 255

Thr Val His Ala Ile Tyr Leu Gln Val Arg His Ala Val Val Asn Ile
            260                 265                 270

Leu Trp Glu Lys Pro Pro Leu Lys Tyr Glu Thr Leu Gln Ala Leu Ala
        275                 280                 285
```

```
Leu Leu Cys Leu Trp Pro Ala Thr Ala Gln Lys Glu Pro Pro Met Asp
    290                 295                 300
Ser Trp Leu Leu Ser Gly Ile Ser Ile Asn His Ala Ile Ile Ala Leu
305                 310                 315                 320
Asp Phe Leu Asn Tyr Ala Pro Ser Glu Val Met Val Asp Asn Glu Thr
                325                 330                 335
Ala Ala Gln Leu Arg Leu Trp Asn Thr Tyr Cys Leu Thr Gln Leu His
            340                 345                 350
Phe Ala Val Gly Asn Ala Arg Pro Phe His Ile Gln Gln Arg Tyr Leu
        355                 360                 365
Asp His Cys Pro Arg Ile Leu Glu His Pro Ala Ala Thr Leu Glu Asp
    370                 375                 380
Ala Arg Val Val Ala Glu Ile Gln Leu Tyr Leu Met Thr Leu Arg Leu
385                 390                 395                 400
Gln Ser Asn Ser Ser Arg Met Arg Leu Ala Asp Leu Asp Tyr Glu Glu
                405                 410                 415
Ile Glu Arg Trp Lys Arg Glu Trp Ala His Leu Phe Cys Lys Lys Pro
            420                 425                 430
Val Leu Val Ser Arg Gly Leu Pro Leu Thr Arg Ala Thr Ala Gly Glu
        435                 440                 445
Ser Ser Thr Leu Glu Leu Ser Leu Trp Phe Cys Gln Thr Leu Leu His
    450                 455                 460
Arg Thr Ala Met Arg Leu Gln Pro Arg Ser Asp Arg Leu Ala Ser Glu
465                 470                 475                 480
Val Leu Gln Thr Ser Arg Leu Ile Ile Ser Arg Phe Leu Gln Ile Arg
                485                 490                 495
Tyr Ser Thr Ala Leu Ser Leu Val Asp Gln Val Tyr Phe Ile Val Gly
            500                 505                 510
Tyr Ala Ala Leu Asn Leu Cys Asp Phe Asn Leu Met Asp Pro Leu Ile
        515                 520                 525
Glu Gln Val Gln Met Phe Leu Leu His Leu Ser Pro Asn Glu Asp His
    530                 535                 540
Ile Ala Tyr Arg Phe Ser Cys Met Val Ala Glu Phe Lys Arg Arg Cys
545                 550                 555                 560
Gly Ser Ala Glu Cys Asn Asp Pro Ser Ser Thr Val Lys Gly Ser Pro
                565                 570                 575
Leu Ser Ser Tyr Gly Asp Ser Arg Lys Met Ser Met Gly Gln Ala Pro
            580                 585                 590
Phe Met Pro Pro Leu Met Asp Gly Met Ile Glu Gly Tyr Gly Phe Glu
        595                 600                 605
Gln Leu Met Pro Glu Val Met Pro Ser Ser Phe Pro Asp Gly Ile Leu
    610                 615                 620
Asn Gly Met Pro Val Thr Gly Leu Ala Ala Tyr Arg Ser Ala Thr Leu
625                 630                 635                 640
Ser Ser Asn Thr Arg Asp Asp Asn Leu Gln Arg Trp Phe Ser Ser Cys
                645                 650                 655
Pro Trp Ala Glu Leu Lys Pro Arg Thr Pro
            660                 665

<210> SEQ ID NO 3
<211> LENGTH: 35
<212> TYPE: PRT
<213> ORGANISM: Aspergillus niger
```

<400> SEQUENCE: 3

Met Thr Ala Cys His Thr Cys Arg Lys Leu Lys Thr Arg Cys Asp Leu
1               5                   10                  15

Asp Pro Arg Gly His Ala Cys Arg Arg Cys Leu Ser Leu Arg Ile Asp
            20                  25                  30

Cys Lys Leu
        35

<210> SEQ ID NO 4
<211> LENGTH: 2542
<212> TYPE: DNA
<213> ORGANISM: Artificial
<220> FEATURE:
<223> OTHER INFORMATION: Synthetic

<400> SEQUENCE: 4

```
gacatggatt ggctggccgc cgtgctgccg tccattagcg tctacccag gtcaagaacg    60
gactggacgg acccataacc aatctaacca agccaattt cgtcaattcc cagctggcga   120
gcacaatccc attcccaggg ttggccgcca actgttaaaa ggcactatgt gtctctccac   180
ctgcccgccc ccctcgatgg cctgcgcgta ataactattc tactgctttt tgcctcttac   240
ttgcctcatt attagtattt tactctactc tccagattgc ctgccagcaa ttggtccaaa   300
gtggactttg tttgatgaca tgactcgaac cgtggacgag atcaaatacg aaacgccttc   360
ttcatgggag cacaagagct ggacgttgc cgaggatggc aggcgactag ctccccattc   420
cgacactgct cgtccgaaag gccgcatacg acgatcgatg actgcctgtc acacatgtcg   480
gaagcttaaa actagatgtg atctagatcc gcgcggtcat gcgtgccgtc gctgtctatc   540
tctaaggtca gaggcactac ctacctgcca gttgaagctt tgtccttctg aacgcgacat   600
gatactagtc gtggaatata actgtcccaa ctttgctgac agtccacaat atctttagaa   660
tcgattgtaa gctgcctgaa acgaccgacc gcttccaaga cagtgctgcg atgtggccag   720
acgccacctc ggcaattccc tccatcgagg agcgcctcac ctccctagaa agatgcatga   780
gggagatgac gggcatgatg cgacagatgc tagatcactc cccaggtttc gcaaatgcct   840
cggttccgca tttgaccaaa agcatcatca cggatgaaac cgcctcgatg agggaagcc   900
cgtcgtcccc cttcctgcct aagcccgttc gcctcattca ggacctccag tccgacttct   960
tcggagaagc agagacttcc cccgttgact cccctctctc cagcgatggt aacgccaagg  1020
gcgctatcga ctctaagcta tccctcaaat tgttgcaaac gtatgggtat acctgattga  1080
caattaccaa aaagctgcta atccttggcg caaatcaggt ttgtcgatca ctttggcgct  1140
tgcgtttcca tttacaatct ctccgacatc cacaacgaca tgaaagcccc cgactcttta  1200
ctgtataata ctgcatgcct tctagcttca cgctatgtac cggggatacc gacatctacc  1260
gtgcatgcta tatccttca agtgcgacat gcagtagtca atattttgtg gaaaaaacca  1320
cccctgaagt atgagaccct ccaagcactt gcacttctct gtctctggcc agcaaccgcc  1380
cagaaagagc cacccatgga cagctggctg ctgagtggta tctcaattaa ccatgcaatt  1440
atcgcgctcg atttcctaaa ctatgcgccc tcggaagtca tggtggacaa tgaaacggct  1500
gcgcagctgc ggctatggaa tacatattgc ttgacacagc tacagtgggt ttcatctaag  1560
atctcccgtc cagaagatag ctaacaagct ttagttttgc ggtcgggaat gcgcgtcctt  1620
tccatatcca gcaaagatac cttgaccact gcccacggat actggagcac ccagcagcaa  1680
ctctggagga cgcaagggtt gtagcagaaa tacagttgta tttgatgaca ttgcggctcc  1740
agagcaatag cagtcgaatg cggttggcgg accttgacta tgaggaaata gagcgatgga  1800
```

| | | | | | |
|---|---|---|---|---|---|
| agagggagtg | ggctcacctt | ttctgtaaga | agcctgttct | tgtttccggg | ggactaccac | 1860 |
| tgacgagagc | aacagctggg | gaaagttcca | cattggagct | gagcctttgg | ttctgccaga | 1920 |
| cactccttca | ccgcacagca | atgaggcttc | agcccagatc | cgacaggctc | gcatctgagg | 1980 |
| ttctgcaaac | ctcacgtctg | ataatatcgc | ggttcctcca | gatccggtac | tctaccgcat | 2040 |
| taagccttgt | cgaccaagtc | tatttcattg | tcggctacgc | tgcactgaat | ctgtgcgatt | 2100 |
| tcaatcttat | ggacccgctt | atcgagcaag | tgcagatgtt | cctgctgcat | ctctccccga | 2160 |
| acgaagacca | catcgcctac | cggttttcgt | gcatggtcgc | cgagttcaag | cggcgatgtg | 2220 |
| gcagtgcgga | atgcaatgac | ccatcatcca | ctgtcaaggg | gtctccgtta | tcatcctacg | 2280 |
| gcgacagtcg | taagatgagc | atggggcaag | caccgttcat | gccaccgctc | atggatggca | 2340 |
| tgatcgaggg | gtacggcttc | gagcaactga | tgccagaagt | catgccgagt | tcctttccgg | 2400 |
| atgggatact | caacggaatg | cctgtgactg | ggctagcagc | gtatcggtca | gcgacgctgt | 2460 |
| aagtaatcga | gatcgggttg | gaaaggacat | gagtgggggt | ggtggtggta | gtagcagtaa | 2520 |
| caccagggat | gataacctgc | ag | | | | 2542 |

<210> SEQ ID NO 5
<211> LENGTH: 665
<212> TYPE: PRT
<213> ORGANISM: Artificial
<220> FEATURE:
<223> OTHER INFORMATION: Synthetic

<400> SEQUENCE: 5

Met Thr Arg Thr Val Asp Glu Ile Lys Tyr Glu Thr Pro Ser Ser Trp
1               5                   10                  15

Glu His Lys Ser Leu Asp Val Ala Glu Asp Gly Arg Arg Leu Ala Pro
            20                  25                  30

His Ser Asp Thr Ala Arg Pro Lys Gly Arg Ile Arg Arg Ser Met Thr
        35                  40                  45

Ala Cys His Thr Cys Arg Lys Leu Lys Thr Arg Cys Asp Leu Asp Pro
    50                  55                  60

Arg Gly His Ala Cys Arg Arg Cys Leu Ser Leu Arg Ile Asp Cys Lys
65                  70                  75                  80

Leu Pro Glu Thr Thr Asp Arg Phe Gln Asp Ser Ala Ala Met Trp Pro
                85                  90                  95

Asp Ala Thr Ser Ala Ile Pro Ser Ile Glu Glu Arg Leu Thr Ser Pro
            100                 105                 110

Glu Arg Cys Met Arg Glu Met Thr Gly Met Met Arg Gln Met Leu Asp
        115                 120                 125

His Ser Pro Gly Phe Ala Asn Ala Ser Val Pro His Leu Thr Lys Ser
    130                 135                 140

Ile Ile Thr Asp Glu Thr Ala Ser Met Glu Gly Ser Pro Ser Ser Pro
145                 150                 155                 160

Phe Leu Pro Lys Pro Val Arg Leu Ile Gln Asp Leu Gln Ser Asp Phe
                165                 170                 175

Phe Gly Glu Ala Glu Thr Ser Pro Val Asp Ser Pro Leu Ser Ser Asp
            180                 185                 190

Gly Asn Ala Lys Gly Ala Ile Asp Ser Lys Leu Ser Leu Lys Leu Leu
        195                 200                 205

Gln Thr Phe Val Asp His Phe Gly Ala Cys Val Ser Ile Tyr Asn Leu
    210                 215                 220

Ser Asp Ile His Asn Asp Met Lys Ala Pro Asp Ser Leu Leu Tyr Asn
225                 230                 235                 240

```
Thr Ala Cys Leu Leu Ala Ser Arg Tyr Val Pro Gly Ile Pro Thr Ser
                245                 250                 255

Thr Val His Ala Ile Tyr Leu Gln Val Arg His Ala Val Val Asn Ile
            260                 265                 270

Leu Trp Glu Lys Pro Pro Leu Lys Tyr Glu Thr Leu Gln Ala Leu Ala
        275                 280                 285

Leu Leu Cys Leu Trp Pro Ala Thr Ala Gln Lys Glu Pro Pro Met Asp
    290                 295                 300

Ser Trp Leu Leu Ser Gly Ile Ser Ile Asn His Ala Ile Ile Ala Leu
305                 310                 315                 320

Asp Phe Leu Asn Tyr Ala Pro Ser Glu Val Met Val Asp Asn Glu Thr
                325                 330                 335

Ala Ala Gln Leu Arg Leu Trp Asn Thr Tyr Cys Leu Thr Gln Leu His
            340                 345                 350

Phe Ala Val Gly Asn Ala Arg Pro Phe His Ile Gln Gln Arg Tyr Leu
        355                 360                 365

Asp His Cys Pro Arg Ile Leu Glu His Pro Ala Ala Thr Leu Glu Asp
    370                 375                 380

Ala Arg Val Val Ala Glu Ile Gln Leu Tyr Leu Met Thr Leu Arg Leu
385                 390                 395                 400

Gln Ser Asn Ser Ser Arg Met Arg Leu Ala Asp Leu Asp Tyr Glu Glu
                405                 410                 415

Ile Glu Arg Trp Lys Arg Glu Trp Ala His Leu Phe Cys Lys Lys Pro
            420                 425                 430

Val Leu Val Ser Arg Gly Leu Pro Leu Thr Arg Ala Thr Ala Gly Glu
        435                 440                 445

Ser Ser Thr Leu Glu Leu Ser Leu Trp Phe Cys Gln Thr Leu Leu His
    450                 455                 460

Arg Thr Ala Met Arg Leu Gln Pro Arg Ser Asp Arg Leu Ala Ser Glu
465                 470                 475                 480

Val Leu Gln Thr Ser Arg Leu Ile Ile Ser Arg Phe Leu Gln Ile Arg
                485                 490                 495

Tyr Ser Thr Ala Leu Ser Leu Val Asp Gln Val Tyr Phe Ile Val Gly
            500                 505                 510

Tyr Ala Ala Leu Asn Leu Cys Asp Phe Asn Leu Met Asp Pro Leu Ile
        515                 520                 525

Glu Gln Val Gln Met Phe Leu Leu His Leu Ser Pro Asn Glu Asp His
    530                 535                 540

Ile Ala Tyr Arg Phe Ser Cys Met Val Ala Glu Phe Lys Arg Arg Cys
545                 550                 555                 560

Gly Ser Ala Glu Cys Asn Asp Pro Ser Ser Thr Val Lys Gly Ser Pro
                565                 570                 575

Leu Ser Ser Tyr Gly Asp Ser Arg Lys Met Ser Met Gly Gln Ala Pro
            580                 585                 590

Phe Met Pro Pro Leu Met Asp Gly Met Ile Glu Gly Tyr Gly Phe Glu
        595                 600                 605

Gln Leu Met Pro Glu Val Met Pro Ser Ser Phe Pro Asp Gly Ile Leu
    610                 615                 620

Asn Gly Met Pro Val Thr Gly Leu Ala Ala Tyr Arg Ser Ala Thr Leu
625                 630                 635                 640

Ser Ser Asn Thr Arg Asp Asp Asn Leu Gln Arg Trp Phe Ser Ser Cys
                645                 650                 655

Pro Trp Ala Glu Leu Lys Pro Arg Thr
            660                 665
```

```
<210> SEQ ID NO 6
<211> LENGTH: 29
<212> TYPE: DNA
<213> ORGANISM: Artificial
<220> FEATURE:
<223> OTHER INFORMATION: Primer

<400> SEQUENCE: 6
cggaattcgc atgctggagg tgcttctaa                              29

<210> SEQ ID NO 7
<211> LENGTH: 33
<212> TYPE: DNA
<213> ORGANISM: Artificial
<220> FEATURE:
<223> OTHER INFORMATION: Primer

<400> SEQUENCE: 7
ttcccaggat tgaggcattt tgaccacgag att                         33

<210> SEQ ID NO 8
<211> LENGTH: 17
<212> TYPE: DNA
<213> ORGANISM: Artificial
<220> FEATURE:
<223> OTHER INFORMATION: Primer

<400> SEQUENCE: 8
taacttccac cgaggtc                                           17

<210> SEQ ID NO 9
<211> LENGTH: 18
<212> TYPE: DNA
<213> ORGANISM: Artificial
<220> FEATURE:
<223> OTHER INFORMATION: Primer

<400> SEQUENCE: 9
cgatcgatga ctgcctgt                                          18

<210> SEQ ID NO 10
<211> LENGTH: 18
<212> TYPE: DNA
<213> ORGANISM: Artificial
<220> FEATURE:
<223> OTHER INFORMATION: Primer

<400> SEQUENCE: 10
agagacacat agtgcctt                                          18

<210> SEQ ID NO 11
<211> LENGTH: 18
<212> TYPE: DNA
<213> ORGANISM: Artificial
<220> FEATURE:
<223> OTHER INFORMATION: Primer

<400> SEQUENCE: 11
gcttatagtc gatagcgc                                          18

<210> SEQ ID NO 12
<211> LENGTH: 18
<212> TYPE: DNA
<213> ORGANISM: Artificial
<220> FEATURE:
<223> OTHER INFORMATION: Primer
```

-continued

```
<400> SEQUENCE: 12
cctctctcca gcgatggt                                                 18

<210> SEQ ID NO 13
<211> LENGTH: 18
<212> TYPE: DNA
<213> ORGANISM: Artificial
<220> FEATURE:
<223> OTHER INFORMATION: Primer

<400> SEQUENCE: 13
atggaataca tactgctt                                                 18

<210> SEQ ID NO 14
<211> LENGTH: 18
<212> TYPE: DNA
<213> ORGANISM: Artificial
<220> FEATURE:
<223> OTHER INFORMATION: Primer

<400> SEQUENCE: 14
atgaaaccca ctgtagct                                                 18

<210> SEQ ID NO 15
<211> LENGTH: 18
<212> TYPE: DNA
<213> ORGANISM: Artificial
<220> FEATURE:
<223> OTHER INFORMATION: Primer

<400> SEQUENCE: 15
tgctcgataa gcgggtcc                                                 18

<210> SEQ ID NO 16
<211> LENGTH: 18
<212> TYPE: DNA
<213> ORGANISM: Artificial
<220> FEATURE:
<223> OTHER INFORMATION: Primer

<400> SEQUENCE: 16
attcttatgg acccgctt                                                 18

<210> SEQ ID NO 17
<211> LENGTH: 20
<212> TYPE: DNA
<213> ORGANISM: Artificial
<220> FEATURE:
<223> OTHER INFORMATION: Primer

<400> SEQUENCE: 17
ccccgggaaa caagaacagg                                               20

<210> SEQ ID NO 18
<211> LENGTH: 20
<212> TYPE: DNA
<213> ORGANISM: Artificial
<220> FEATURE:
<223> OTHER INFORMATION: Primer

<400> SEQUENCE: 18
gttggcggac cttgactatg                                               20
```

```
<210> SEQ ID NO 19
<211> LENGTH: 22
<212> TYPE: DNA
<213> ORGANISM: Artificial
<220> FEATURE:
<223> OTHER INFORMATION: Primer

<400> SEQUENCE: 19
acagctacag tgggtttcat ct                                            22

<210> SEQ ID NO 20
<211> LENGTH: 19
<212> TYPE: DNA
<213> ORGANISM: Artificial
<220> FEATURE:
<223> OTHER INFORMATION: Primer

<400> SEQUENCE: 20
agtcaacggg ggaagtctc                                                19

<210> SEQ ID NO 21
<211> LENGTH: 20
<212> TYPE: DNA
<213> ORGANISM: Artificial
<220> FEATURE:
<223> OTHER INFORMATION: Primer

<400> SEQUENCE: 21
ctagcagcgt atcggtcagc                                               20

<210> SEQ ID NO 22
<211> LENGTH: 19
<212> TYPE: DNA
<213> ORGANISM: Artificial
<220> FEATURE:
<223> OTHER INFORMATION: Primer

<400> SEQUENCE: 22
cttggaaaag aaacgatag                                                19

<210> SEQ ID NO 23
<211> LENGTH: 19
<212> TYPE: DNA
<213> ORGANISM: Artificial
<220> FEATURE:
<223> OTHER INFORMATION: Primer

<400> SEQUENCE: 23
aacgtacgct ttcctccatt                                               19

<210> SEQ ID NO 24
<211> LENGTH: 21
<212> TYPE: DNA
<213> ORGANISM: Artificial
<220> FEATURE:
<223> OTHER INFORMATION: Primer

<400> SEQUENCE: 24
gggtccgtcc agtccgttct t                                             21

<210> SEQ ID NO 25
<211> LENGTH: 24
<212> TYPE: DNA
<213> ORGANISM: Artificial
<220> FEATURE:
<223> OTHER INFORMATION: Primer
```

```
<400> SEQUENCE: 25
agcggataac aatttcacac agga                                    24

<210> SEQ ID NO 26
<211> LENGTH: 17
<212> TYPE: DNA
<213> ORGANISM: Artificial
<220> FEATURE:
<223> OTHER INFORMATION: Primer

<400> SEQUENCE: 26
gttttcccag tcacgac                                            17

<210> SEQ ID NO 27
<211> LENGTH: 19
<212> TYPE: DNA
<213> ORGANISM: Artificial
<220> FEATURE:
<223> OTHER INFORMATION: Primer

<400> SEQUENCE: 27
tcatccctgg tgttactgc                                          19

<210> SEQ ID NO 28
<211> LENGTH: 17
<212> TYPE: DNA
<213> ORGANISM: Artificial
<220> FEATURE:
<223> OTHER INFORMATION: Primer

<400> SEQUENCE: 28
catggattgg ctggccg                                            17

<210> SEQ ID NO 29
<211> LENGTH: 18
<212> TYPE: DNA
<213> ORGANISM: Artificial
<220> FEATURE:
<223> OTHER INFORMATION: Primer

<400> SEQUENCE: 29
tactctccag attgcctg                                           18

<210> SEQ ID NO 30
<211> LENGTH: 18
<212> TYPE: DNA
<213> ORGANISM: Artificial
<220> FEATURE:
<223> OTHER INFORMATION: Primer

<400> SEQUENCE: 30
tgagatacca ctcagcag                                           18

<210> SEQ ID NO 31
<211> LENGTH: 18
<212> TYPE: DNA
<213> ORGANISM: Artificial
<220> FEATURE:
<223> OTHER INFORMATION: Primer

<400> SEQUENCE: 31
tgcacttctc tgtctctg                                           18
```

```
<210> SEQ ID NO 32
<211> LENGTH: 18
<212> TYPE: DNA
<213> ORGANISM: Artificial
<220> FEATURE:
<223> OTHER INFORMATION: Primer

<400> SEQUENCE: 32
gacttctggc atcagttg                                                 18

<210> SEQ ID NO 33
<211> LENGTH: 18
<212> TYPE: DNA
<213> ORGANISM: Artificial
<220> FEATURE:
<223> OTHER INFORMATION: Primer

<400> SEQUENCE: 33
ctcatggatg gcatgatc                                                 18

<210> SEQ ID NO 34
<211> LENGTH: 33
<212> TYPE: PRT
<213> ORGANISM: Aspergillus niger

<400> SEQUENCE: 34

Met Thr Ala Cys His Thr Cys Arg Lys Leu Lys Thr Arg Cys Asp Leu
1               5                   10                  15

Asp Pro Arg Gly His Ala Cys Arg Arg Cys Leu Ser Leu Arg Ile Asp
            20                  25                  30

Cys

<210> SEQ ID NO 35
<211> LENGTH: 20
<212> TYPE: DNA
<213> ORGANISM: Artificial
<220> FEATURE:
<223> OTHER INFORMATION: Primer

<400> SEQUENCE: 35
atgacygcyt gycayacytg                                               20

<210> SEQ ID NO 36
<211> LENGTH: 20
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (9)..(9)
<223> OTHER INFORMATION: n is a, c, g, or t

<400> SEQUENCE: 36
arrcancgnc grcargcrtg                                               20

<210> SEQ ID NO 37
<211> LENGTH: 20
<212> TYPE: DNA
<213> ORGANISM: Artificial
<220> FEATURE:
<223> OTHER INFORMATION: Primer
```

```
<400> SEQUENCE: 37
atgactgcct gtcacacatg                                          20

<210> SEQ ID NO 38
<211> LENGTH: 20
<212> TYPE: DNA
<213> ORGANISM: Artificial
<220> FEATURE:
<223> OTHER INFORMATION: Primer

<400> SEQUENCE: 38
agacagcgac ggcacgcatg                                          20

<210> SEQ ID NO 39
<211> LENGTH: 21
<212> TYPE: DNA
<213> ORGANISM: Artificial
<220> FEATURE:
<223> OTHER INFORMATION: Primer

<400> SEQUENCE: 39
caccgagttt taagcttgcg g                                        21

<210> SEQ ID NO 40
<211> LENGTH: 20
<212> TYPE: DNA
<213> ORGANISM: Artificial
<220> FEATURE:
<223> OTHER INFORMATION: Primer

<400> SEQUENCE: 40
gcgatcttga tccacgaggg                                          20

<210> SEQ ID NO 41
<211> LENGTH: 21
<212> TYPE: DNA
<213> ORGANISM: Artificial
<220> FEATURE:
<223> OTHER INFORMATION: Primer

<400> SEQUENCE: 41
cgggatgaat tgtagagagg c                                        21

<210> SEQ ID NO 42
<211> LENGTH: 25
<212> TYPE: DNA
<213> ORGANISM: Artificial
<220> FEATURE:
<223> OTHER INFORMATION: Primer

<400> SEQUENCE: 42
cgcaagctta aaactcggtg cgatc                                    25

<210> SEQ ID NO 43
<211> LENGTH: 20
<212> TYPE: DNA
<213> ORGANISM: Artificial
<220> FEATURE:
<223> OTHER INFORMATION: Primer

<400> SEQUENCE: 43
cctcgtggat caagatcgca                                          20
```

```
<210> SEQ ID NO 44
<211> LENGTH: 22
<212> TYPE: DNA
<213> ORGANISM: Artificial
<220> FEATURE:
<223> OTHER INFORMATION: Primer

<400> SEQUENCE: 44
gatgaaaaga ataatcggcg ag                                              22

<210> SEQ ID NO 45
<211> LENGTH: 21
<212> TYPE: DNA
<213> ORGANISM: Artificial
<220> FEATURE:
<223> OTHER INFORMATION: Primer

<400> SEQUENCE: 45
cgcggcacac taccccgtt g                                                21

<210> SEQ ID NO 46
<211> LENGTH: 22
<212> TYPE: DNA
<213> ORGANISM: Artificial
<220> FEATURE:
<223> OTHER INFORMATION: Primer

<400> SEQUENCE: 46
atctagctca agcattagcg gc                                              22

<210> SEQ ID NO 47
<211> LENGTH: 21
<212> TYPE: DNA
<213> ORGANISM: Artificial
<220> FEATURE:
<223> OTHER INFORMATION: Primer

<400> SEQUENCE: 47
aatttcggcc ctttagtgtc c                                               21

<210> SEQ ID NO 48
<211> LENGTH: 2931
<212> TYPE: DNA
<213> ORGANISM: Aspergillus oryzae
<220> FEATURE:
<221> NAME/KEY: Intron
<222> LOCATION: (1028)..(1135)
<220> FEATURE:
<221> NAME/KEY: Intron
<222> LOCATION: (1538)..(1591)
<220> FEATURE:
<221> NAME/KEY: Intron
<222> LOCATION: (2018)..(2066)
<220> FEATURE:
<221> NAME/KEY: Intron
<222> LOCATION: (2297)..(2347)

<400> SEQUENCE: 48
gatatctcat gatctgcgtg atcggcttgc ctcctatctt agatcacccg ggcttcttca      60
aatcagcaac aacgctcaga catgtcccct gagaggtgat ccaaatcata cacgagagaa     120
cgcggaaacg caaattaagg atgagcgaaa aagagaaaaa aatccgttgt tcctgagtca     180
tgacgaatga gcaaaagtca aacacacctt ctgcttttgg ggggtatgcc cgatcacaat     240
cttcaacccg ccatgataag agacacacgc tatcgacaaa tcaccggagg tcaagattag     300
tggcagtcct tagctaattt caggtcggcg tcaaccttag ccaacccaac ccaaccccct     360
catggaagcg ggactcccta tggagccggc ttacatcggg cgcactgcaa tggcgcacgt     420
```

| | | | | | |
|---|---|---|---|---|---|
| caatcaaccc | ctctcttgtt | gcagtgccta | gtatgccaaa | ccacccttc | tattcttcta | 480 |
| gaaaccacac | cctagagact | cggatctaca | cggattggtt | ggaatgctcc | gattagttgg | 540 |
| catttacccc | aggtcaaaat | ggataatcaa | tctaacggag | tctatttcgt | caactgcctg | 600 |
| ccagctagca | caatctcctc | ttcacgcccg | gccgtgggct | gttaaaaggg | tcaattccct | 660 |
| ccccacctgt | gtggattctc | tatgatttgc | acgggatctg | acttggtttc | cacaattctt | 720 |
| cttgctctca | gcttgttcta | ctcgccgatt | attcttttca | tcaacgcggc | acactacccc | 780 |
| cgttgtctga | tgtcatgact | agaactactg | ttgaacctat | caaatatgag | gcccctcgt | 840 |
| gggagcataa | gagcgtgcat | gtgtccgacg | accacaggag | aatcatcccc | aatgtcggcg | 900 |
| acgacgcgac | gcgcccaaag | ggccgcatta | gacgttcaat | gaccgcttgt | aatacctgcc | 960 |
| gcaagcttaa | aactcggtgc | gatcttgatc | cacgagggca | tgcatgccgg | cggtgtctat | 1020 |
| ctttaaggtc | gggtgccacc | gttatccact | ttgtcaaatc | tcttacgtca | aatggggga | 1080 |
| tcccatgtcc | tgccaagacc | aaataagcct | tcttgagta | ctaatgtttc | ataggatcg | 1140 |
| actgtcagct | ccccgagacg | agtgagcgct | tcaggacag | tactccaatg | tggtcagacg | 1200 |
| caacgacagc | tatcccctcc | atcgaggagc | gtctcacttc | cctagagagg | agtatgagag | 1260 |
| agatgaccgg | catgcttcgg | cagatcttga | atcaatcacc | aagcgtctct | aatatctccg | 1320 |
| tccctccgct | agctcggagt | gttcatacgg | aagaaacggc | ctccattgaa | ggaaactcat | 1380 |
| tcggtccttt | cctacctaaa | cccgttcggc | taattcagga | cctccaatct | gagtttttg | 1440 |
| gggagacaaa | ccgcatccct | gttgaatctc | ctttcttggg | taacagtttt | gagaagggta | 1500 |
| tcttagattc | taagttgtct | ctcaagttgg | tacagctgta | tggtcactcg | tcatgtccat | 1560 |
| ctgcctctat | agccgctaat | gcttgagcta | gatttgtgga | taatttcggc | cctttagtgt | 1620 |
| ccataaataa | tcagtcggac | ttccacaacg | agatgaggaa | caccgattcg | ttgttatata | 1680 |
| gtactgcctg | tcttctggcc | tcccgatatg | tgccaggcat | accaccaccg | attgtccata | 1740 |
| ccatgaacct | ccaagttcga | cataaggcag | tcaatctgct | gtgggaagaa | ccgcctttga | 1800 |
| aatacgaatc | gctccaggca | ctcgcccttc | tttgtttatg | gccagcggcg | ggtcaaaagg | 1860 |
| agttccccat | agatggctgg | ttactgagcg | ggactgcaat | caatcatgcc | ctcgtctcct | 1920 |
| ttgacttcct | caatcatgtg | ccttcagagc | ttctcattga | taacgatatc | gccgctcaat | 1980 |
| tgcggctctg | gaacgctttc | tgtttaacac | agttacagta | ggtacaacat | ttccggctta | 2040 |
| actccaactt | gctaatgcag | aaatagtttc | gctgttggca | acgcacgtcc | attccattta | 2100 |
| ccacagagat | atctcgatta | ttgcccacga | cttcttgagc | accccgctgc | aacagttgag | 2160 |
| gatggcaagg | tcgtagcaga | gatccagttg | tacttgatca | cattgcgact | ccaagccaac | 2220 |
| gagcaacgta | tgcgattcgc | ggaggttgaa | tacgaagaga | ttgaacgatg | aaagttgaa | 2280 |
| tgggcccatc | ttcttggtaa | ggttaagcaa | cgaggaccat | ctcatataaa | tgctaactat | 2340 |
| tcaacagctg | gtgatgaaaa | ttcaacattt | gagcttagtc | tctggttctg | tcaaatcctc | 2400 |
| ctgcatcgga | cagcaatgag | gttccaagcg | gagtctgaga | gactcacgtc | ggaaattctc | 2460 |
| caaggatcgc | gcttgatcat | ctcgaaattc | ctgcaactcc | gatttgtcac | cgctctaaga | 2520 |
| gtggtcgatc | aggcgtactt | catcgtcggt | tatgccgctc | taaatctttg | cgacttcaac | 2580 |
| ttcctcgacc | ccctcattga | ccagatccag | atgtttctgc | tgcatctgtc | gccaaacgaa | 2640 |
| gaccacatcg | cataccggtt | ttcgtgcatg | atagccgagt | tcaagcgtcg | ctgtgccgaa | 2700 |
| tgcaacgacc | cttgcagcgc | agtcgacggt | tctcaatgct | cgttcggaga | tgcccggaag | 2760 |
| atgagcatgg | aacaggtaca | attcgtgcca | ccactagtag | atagcatgat | tgggggatat | 2820 | agcgctctgg aacagctgat ccctgaggtc atgccacact catttccgga aagtgtcata 2880 agtggcatgg ctgtgactga agccatccct gtgggatcgg cgccatacta g 2931

<210> SEQ ID NO 49
<211> LENGTH: 624
<212> TYPE: PRT
<213> ORGANISM: Aspergillus oryzae

<400> SEQUENCE: 49

```
Met Thr Arg Thr Thr Val Glu Pro Ile Lys Tyr Glu Ala Pro Ser Trp
1               5                   10                  15

Glu His Lys Ser Val His Val Ser Asp Asp His Gly Arg Ile Ile Pro
            20                  25                  30

Asn Val Gly Asp Asp Ala Thr Arg Pro Lys Gly Arg Ile Arg Arg Ser
        35                  40                  45

Met Thr Ala Cys Asn Thr Cys Arg Lys Leu Lys Thr Arg Cys Asp Leu
    50                  55                  60

Asp Pro Arg Gly His Ala Cys Arg Arg Cys Leu Ser Leu Arg Ile Asp
65                  70                  75                  80

Cys Gln Leu Pro Glu Thr Ser Glu Arg Phe Gln Asp Ser Thr Pro Met
                85                  90                  95

Trp Ser Asp Ala Thr Thr Ala Ile Pro Ser Ile Glu Glu Arg Leu Thr
            100                 105                 110

Ser Leu Glu Arg Ser Met Arg Glu Met Thr Gly Met Leu Arg Gln Ile
        115                 120                 125

Leu Asn Gln Ser Pro Ser Val Ser Asn Ile Ser Val Pro Pro Leu Ala
    130                 135                 140

Arg Ser Val His Thr Glu Glu Thr Ala Ser Ile Glu Gly Asn Ser Phe
145                 150                 155                 160

Gly Pro Phe Leu Pro Lys Pro Val Arg Leu Ile Gln Asp Leu Gln Ser
                165                 170                 175

Glu Phe Phe Gly Glu Thr Asn Arg Ile Pro Val Glu Ser Pro Phe Leu
            180                 185                 190

Gly Asn Ser Phe Glu Lys Gly Ile Leu Asp Ser Lys Leu Ser Leu Lys
        195                 200                 205

Leu Val Gln Leu Phe Val Asp Asn Phe Gly Pro Leu Val Ser Ile Asn
    210                 215                 220

Asn Gln Ser Asp Phe His Asn Glu Met Arg Asn Thr Asp Ser Leu Leu
225                 230                 235                 240

Tyr Ser Thr Ala Cys Leu Leu Ala Ser Arg Tyr Val Pro Gly Ile Pro
                245                 250                 255

Pro Pro Ile Val His Thr Met Asn Leu Gln Val Arg His Lys Ala Val
            260                 265                 270

Asn Leu Leu Trp Glu Glu Pro Pro Leu Lys Tyr Glu Ser Leu Gln Ala
        275                 280                 285

Leu Ala Leu Leu Cys Leu Trp Pro Ala Ala Gly Gln Lys Glu Phe Pro
    290                 295                 300

Ile Asp Gly Trp Leu Leu Ser Gly Thr Ala Ile Asn His Ala Leu Val
305                 310                 315                 320

Ser Phe Asp Phe Leu Asn His Val Pro Ser Glu Leu Leu Ile Asp Asn
                325                 330                 335

Asp Ile Ala Ala Gln Leu Arg Leu Trp Asn Ala Phe Cys Leu Thr Gln
            340                 345                 350

Leu His Phe Ala Val Gly Asn Ala Arg Pro Phe His Leu Pro Gln Arg
        355                 360                 365
```

| | | | | | | | | | | | | |
|---|---|---|---|---|---|---|---|---|---|---|---|---|
|Tyr|Leu|Asp|Tyr|Cys|Pro|Arg|Leu|Leu|Glu|His|Pro|Ala Ala Thr Val|
| |370| | | |375| | | |380| | | |

| | | | | | | | | | | | | |
|---|---|---|---|---|---|---|---|---|---|---|---|---|
|Glu|Asp|Gly|Lys|Val|Val|Ala|Glu|Ile|Gln|Leu|Tyr|Leu Ile Thr Leu|
|385| | | | |390| | | |395| | |400|

Arg Leu Gln Ala Asn Glu Gln Arg Met Arg Phe Ala Glu Val Glu Tyr
    405                 410                 415

Glu Glu Ile Glu Arg Trp Lys Val Glu Trp Ala His Leu Leu Ala Gly
        420                 425                 430

Asp Glu Asn Ser Thr Phe Glu Leu Ser Leu Trp Phe Cys Gln Ile Leu
            435                 440                 445

Leu His Arg Thr Ala Met Arg Phe Gln Ala Glu Ser Glu Arg Leu Thr
450                 455                 460

Ser Glu Ile Leu Gln Gly Ser Arg Leu Ile Ile Ser Lys Phe Leu Gln
465                 470                 475                 480

Leu Arg Phe Val Thr Ala Leu Arg Val Val Asp Gln Ala Tyr Phe Ile
                485                 490                 495

Val Gly Tyr Ala Ala Leu Asn Leu Cys Asp Phe Asn Phe Leu Asp Pro
            500                 505                 510

Leu Ile Asp Gln Ile Gln Met Phe Leu Leu His Leu Ser Pro Asn Glu
        515                 520                 525

Asp His Ile Ala Tyr Arg Phe Ser Cys Met Ile Ala Glu Phe Lys Arg
    530                 535                 540

Arg Cys Ala Glu Cys Asn Asp Pro Cys Ser Ala Val Asp Gly Ser Gln
545                 550                 555                 560

Cys Ser Phe Gly Asp Ala Arg Lys Met Ser Met Glu Gln Val Gln Phe
                565                 570                 575

Val Pro Pro Leu Val Asp Ser Met Ile Gly Gly Tyr Ser Ala Leu Glu
            580                 585                 590

Gln Leu Ile Pro Glu Val Met Pro His Ser Phe Pro Glu Ser Val Ile
        595                 600                 605

Ser Gly Met Ala Val Thr Glu Ala Ile Pro Val Gly Ser Ala Pro Tyr
    610                 615                 620

<210> SEQ ID NO 50
<211> LENGTH: 6015
<212> TYPE: DNA
<213> ORGANISM: Artificial
<220> FEATURE:
<223> OTHER INFORMATION: pDV8 plasmid

<400> SEQUENCE: 50

```
gaatacacgg aattcctcga gtaccattta attctatttg tgtttgatcg agacctaata    60
cagcccctac aacgaccatc aaagtcgtat agctaccagt gaggaagtgg actcaaatcg   120
acttcagcaa catctcctgg ataaacttta agcctaaact atacagaata agataggtgg   180
agagcttata ccgagctccc aaatctgtcc agatcatggt tgaccggtgc ctggatcttc   240
ctatagaatc atccttattc gttgacctag ctgattctgg agtgacccag agggtcatga   300
cttgagccta aaatccgccg cctccaccat ttgtagaaaa atgtgacgaa ctcgtgagct   360
ctgtacagtg accggtgact ctttctggca tgcggagaga cggacggacg cagagagaag   420
ggctgagtaa taagccactg ccagacagc tctggcggct ctgaggtgca gtggatgatt    480
attaatccgg gaccggccgc cctccgccc cgaagtggaa aggctggtgt gcccctcgtt    540
gaccaagaat ctattgcatc atcggagaat atggagcttc atcgaatcac cggcagtaag   600
cgaaggagaa tgtgaagcca ggggtgtata gccgtcggcg aaatagcatg ccattaacct   660
```

| | |
|---|---|
| aggtacagaa gtccaattgc ttccgatctg gtaaaagatt cacgagatag taccttctcc | 720 |
| gaagtaggta gagcgagtac ccggcgcgta agctccctaa ttggcccatc cggcatctgt | 780 |
| agggcgtcca aatatcgtgc ctctcctgct ttgcccggtg tatgaaaccg gaaaggccgc | 840 |
| tcaggagctg ccagcggcg cagaccggga acacaagctg gcagtcgacc catccggtgc | 900 |
| tctgcactcg acctgctgag gtccctcagt ccctggtagg cagctttgcc ccgtctgtcc | 960 |
| gcccggtgtg tcggcggggt tgacaaggtc gttgcgtcag tccaacattt gttgccatat | 1020 |
| tttcctgctc tccccaccag ctgtagatct tggtggcgtg aaactcccgc acctcttcgg | 1080 |
| ccagcgcctt gtagaagcgc gtatggcttc gtaccccggc catcaacacg cgtctgcgtt | 1140 |
| cgaccaggct gcgcgttctc gcggccatag caaccgacgt acggcgttgc gccctcgccg | 1200 |
| gcagcaagaa gccacggaag tccgcccgga gcagaaaatg cccacgctac tgcgggttta | 1260 |
| tatagacggt ccccacggga tggggaaaac caccaccacg caactgctgg tggccctggg | 1320 |
| ttcgcgcgac gatatcgtct acgtacccga gccgatgact tactggcggg tgctgggggc | 1380 |
| ttccgagaca atcgcgaaca tctacaccac acaacaccgc ctcgaccagg gtgagatatc | 1440 |
| ggccggggac gcggcggtgg taatgacaag cgcccagata acaatgggca tgccttatgc | 1500 |
| cgtgaccgac gccgttctgg ctcctcatat cggggggggag gctgggagct cacatgcccc | 1560 |
| gcccccggcc ctcaccctca tcttcgaccg ccatcccatc gccgccctcc tgtgctaccc | 1620 |
| ggccgcgcgg taccttatgg gcagcatgac cccccaggcc gtgctggcgt tcgtggccct | 1680 |
| catcccgccg accttgcccg gcaccaacat cgtgcttggg gcccttccgg aggacagaca | 1740 |
| catcgaccgc ctggccaaac gccagcgccc cggcgagcgg ctggacctgg ctatgctggc | 1800 |
| tgcgattcgc cgcgtttacg ggctacttgc caatacggtg cggtatctgc agtgcggcgg | 1860 |
| gtcgtggcgg gaggactggg gacagctttc ggggacggcc gtgccgcccc agggtgccga | 1920 |
| gccccagagc aacgcgggcc cacgacccca tatcggggac acgttattta ccctgtttcg | 1980 |
| gggccccgag ttgctggccc ccaacggcga cctgtataac gtgtttgcct gggccttgga | 2040 |
| cgtcttggcc aaacgcctcc gttccatgca cgtctttatc ctggattacg accaatcgcc | 2100 |
| cgccggctgc cgggacgccc tgctgcaact tacctccggg atggtccaga cccacgtcac | 2160 |
| caccccggc tccataccga cgatatgcga cctggcgcgc acgtttgccc gggagatggg | 2220 |
| ggaggctaac tgaaacacgg aaggagacaa taccggaagg aacccgcgct atccggatcc | 2280 |
| acttaacgtt actgaaatca tcaaacagct tgacgaatct ggatataaga tcgttggtgt | 2340 |
| cgatgtcagc tccggagttg agacaaatgg tgttcaggat ctcgataaga tacgttcatt | 2400 |
| tgtccaagca gcaaagagtg ccttctagtg atttaatagc tccatgtcaa caagaataaa | 2460 |
| acgcgttttc gggtttacct cttccagata cagctcatct gcaatgcatt aatgcattga | 2520 |
| ctgcaaccta gtaacgcctt caggctccgg cgaagagaag aatagcttag cagagctatt | 2580 |
| ttcattttcg ggagacgaga tcaagcagat caacggtcgt caagagacct acgagactga | 2640 |
| ggaatccgct cttggctcca cgcgactata tatttgtctc taattgtact ttgacatgct | 2700 |
| cctcttcttt actctgatag cttgactatg aaaattccgt caccagccct gggttcgcaa | 2760 |
| agataattgc atgtttcttc cttgaactct caagcctaca ggacacacat tcatcgtagg | 2820 |
| tataaacctc gaaatcattc ctactaagat ggtatacaat agtaaccatg catggttgcc | 2880 |
| tagtgaatgc tccgtaacac ccaatacgcc ggccgaaact tttttacaac tctcctatga | 2940 |
| gtcgtttacc cagaatgcac aggtacactt gtttagaggt aatccttctt tctagaagtc | 3000 |
| ctcgtgtact gtgtaagcgc ccactccaca tctccactcg acctgcaggc atgcaagctt | 3060 |

-continued

```
ggcgtaatca tggtcatagc tgtttcctgt gtgaaattgt tatccgctca caattccaca    3120
caacatacga gccggaagca taaagtgtaa agcctggggt gcctaatgag tgagctaact    3180
cacattaatt gcgttgcgct cactgcccgc tttccagtcg ggaaacctgt cgtgccagag    3240
cggccgctct gcattaatga atcggccaac gcgcggggag aggcggtttg cgtattgggc    3300
gctcttccgc ttcctcgctc actgactcgc tgcgctcggt cgttcggctg cggcgagcgg    3360
tatcagctca ctcaaaggcg gtaatacggt tatccacaga atcaggggat aacgcaggaa    3420
agaacatgtg agcaaaaggc cagcaaaagg ccaggaaccg taaaaaggcc gcgttgctgg    3480
cgtttttcca taggctccgc cccccctgacg agcatcacaa aaatcgacgc tcaagtcaga    3540
ggtggcgaaa cccgacagga ctataaagat accaggcgtt tccccctgga agctccctcg    3600
tgcgctctcc tgttccgacc ctgccgctta ccggatacct gtccgccttt ctcccttcgg    3660
gaagcgtggc gctttctcat agctcacgct gtaggtatct cagttcggtg taggtcgttc    3720
gctccaagct gggctgtgtg cacgaacccc ccgttcagcc cgaccgctgc gccttatccg    3780
gtaactatcg tcttgagtcc aacccggtaa gacacgactt atcgccactg gcagcagcca    3840
ctggtaacag gattagcaga gcgaggtatg taggcggtgc tacagagttc ttgaagtggt    3900
ggcctaacta cggctacact agaaggacag tatttggtat ctgcgctctg ctgaagccag    3960
ttaccttcgg aaaaagagtt ggtagctctt gatccggcaa acaaaccacc gctggtagcg    4020
gtggtttttt tgtttgcaag cagcagatta cgcgcagaaa aaaggatct caagaagatc    4080
ctttgatctt ttctacgggg tctgacgctc agtggaacga aaactcacgt taagggattt    4140
tggtcatgag attatcaaaa aggatcttca cctagatcct tttaaattaa aatgaagtt    4200
ttaaatcaat ctaaagtata tatgagtaaa cttggtctga cagttaccaa tgcttaatca    4260
gtgaggcacc tatctcagcg atctgtctat ttcgttcatc catagttgcc tgactccccg    4320
tcgtgtagat aactacgata cgggagggct taccatctgg ccccagtgct gcaatgatac    4380
cgcgagaccc acgctcaccg gctccagatt tatcagcaat aaaccagcca gccggaaggg    4440
ccgagcgcag aagtggtcct gcaactttat ccgcctccat ccagtctatt aattgttgcc    4500
gggaagctag agtaagtagt tcgccagtta atagtttgcg caacgttgtt gccattgcta    4560
caggcatcgt ggtgtcacgc tcgtcgtttg gtatggcttc attcagctcc ggttcccaac    4620
gatcaaggcg agttacatga tcccccatgt tgtgcaaaaa agcggttagc tccttcggtc    4680
ctccgatcgt tgtcagaagt aagttggccg cagtgttatc actcatggtt atggcagcac    4740
tgcataattc tcttactgtc atgccatccg taagatgctt ttctgtgact ggtgagtact    4800
caaccaagtc attctgagaa tagtgtatgc ggcgaccgag ttgctcttgc ccggcgtcaa    4860
tacgggataa taccgcgcca catagcagaa ctttaaaagt gctcatcatt ggaaaacgtt    4920
cttcggggcg aaaactctca aggatcttac cgctgttgag atccagttcg atgtaaccca    4980
ctcgtgcacc caactgatct tcagcatctt ttactttcac cagcgtttct gggtgagcaa    5040
aaacaggaag gcaaaatgcc gcaaaaaagg gaataagggc gacacggaaa tgttgaatac    5100
tcatactctt cctttttcaa tattattgaa gcatttatca gggttattgt ctcatgagcg    5160
gatacatatt tgaatgtatt tagaaaaata aacaaatagg ggttccgcgc acatttcccc    5220
gaaaagtgcc acctgacgtc taagaaacca ttattatcat gacattaacc tataaaaata    5280
ggcgtatcac gaggcccttt cgtctcgcgc gtttcggtga tgacggtgaa aacctctgac    5340
acatgcagct cccggagacg gtcacagctt gtctgtaagc ggatgccggg agcagacaag    5400
cccgtcaggg cgcgtcagcg ggtgttggcg ggtgtcgggg ctggcttaac tatgcggcat    5460
```

-continued

```
cagagcagat tgtactgaga gtgcaccata tcgacgctct cccttatgcg actcctgcat    5520
taggaagcag cccagtagta ggttgaggcc gttgagcacc gccgccgcaa ggaatggtgc    5580
atgcaaggag atggcgccca acagtccccc ggccacgggg cctgccacca tacccacgcc    5640
gaaacaagcg ctcatgagcc cgaagtggcg agcccgatct tccccatcgg tgatgtcggc    5700
gatataggcg ccagcaaccg cacctgtggc gccggtgatg ccggccacga tgcgtccggc    5760
gtagaggatc tggctagcga tgaccctgct gattggttcg ctgaccattt ccggggtgcg    5820
gaacggcgtt accagaaact cagaaggttc gtccaaccaa accgactctg acggcagttt    5880
acgagagaga tgatagggtc tgcttcagta agccagatgc tacacaatta ggcttgtaca    5940
tattgtcgtt agaacgcggc tacaattaat acataacctt atgtatcata cacatacgat    6000
ttaggtgaca ctata                                                     6015
```

<210> SEQ ID NO 51
<211> LENGTH: 18
<212> TYPE: DNA
<213> ORGANISM: Artificial
<220> FEATURE:
<223> OTHER INFORMATION: Primer

<400> SEQUENCE: 51
cgcgcgtatc ctattgcc    18

<210> SEQ ID NO 52
<211> LENGTH: 20
<212> TYPE: DNA
<213> ORGANISM: Artificial
<220> FEATURE:
<223> OTHER INFORMATION: Primer

<400> SEQUENCE: 52
gccggaaatg ttgtacctac    20

<210> SEQ ID NO 53
<211> LENGTH: 80
<212> TYPE: DNA
<213> ORGANISM: Aspergillus oryzae

<400> SEQUENCE: 53
atgaccgctt gtcatacctg ccgcaagctt aaaactcggt gcgatcttga tccacgaggg    60
catgcctgcc gccgctgcct    80

<210> SEQ ID NO 54
<211> LENGTH: 80
<212> TYPE: DNA
<213> ORGANISM: Aspergillus oryzae

<400> SEQUENCE: 54
atgactgctt gccacacctg ccgcaagctt aaaactcggt gcgatcttga tccacgaggg    60
catgcctgcc gccgctgcct    80

US 8,426,164 B2

FUNGAL TRANSCRIPTIONAL ACTIVATOR USEFUL IN METHODS FOR PRODUCING POLYPEPTIDES

CROSS-REFERENCE TO RELATED APPLICATIONS

This application is a divisional of U.S. application Ser. No. 10/729,172 filed Dec. 5, 2003 which is a divisional of U.S. application Ser. No. 09/525,305 filed Mar. 14, 2000, now U.S. Pat. No. 6,806,062, which is a continuation-in-part of U.S. application Ser. No. 09/411,925 filed Oct. 4, 1999, now abandoned, which claims priority or the benefit under 35 U.S.C. 119 of Danish Application No. PA 1998 01258 filed Oct. 5, 1998 and U.S. Provisional Application No. 60/103,945 filed Oct. 13, 1998, the contents of which are fully incorporated herein by reference.

BACKGROUND OF THE INVENTION

1. Field of the Invention

The present invention relates to isolated nucleic acid sequences encoding polypeptides having transcriptional activation activity and to the polypeptides. The invention also relates to nucleic acid constructs, vectors and host cells comprising the nucleic acid sequences. The invention further relates to host cells useful for the production of polypeptides in which the production or function of the transcriptional activator has been altered, as well as to methods for producing the polypeptides.

2. Description of the Related Art

The use of recombinant host cells in the expression of heterologous proteins has in recent years greatly simplified the production of large quantities of commercially valuable proteins which otherwise are obtainable only by purification from their native sources. Currently, there is a varied selection of expression systems from which to choose for the production of any given protein, including eubacterial and eukaryotic hosts. The selection of an appropriate expression system often depends not only on the ability of the host cell to produce adequate yields of the protein in an active state, but, to a large extent, may also be governed by the intended end use of the protein.

One problem frequently encountered is the high level of proteolytic enzymes produced by a given host cell or present in the culture medium. One suggestion has been to provide host organisms deprived of the ability to produce specific proteolytic compounds. For example, WO 90/00192 (Genencor, Inc.) describes filamentous fungal hosts incapable of secreting enzymatically active aspartic proteinase. EP 574 347 (Ciba Geigy AG) describes *Aspergillus* hosts defective in a serine protease of the subtilisin-type. WO 98/12300 (Novo Nordisk A/S) describes hosts defective in a metalloprotease and an alkaline protease. WO 97/12045 (Genencor, Inc.) describes yeast and bacterial host systems, which are rendered protease deficient resulting from a disruption of a promoter sequence involved in the regulation of a protease gene.

Mattern, I. E., et al., (1992. Mol Gen Genet 234:332-336) describe a mutant strain of *Aspergillus niger*, which was shown to have only 1 to 2% of the extracellular protease activity of the parent strain, apparently due to a deficiency of at least two proteases, aspergillopepsin A and aspergillopepsin B. It was suggested that the protease deficient phenotype could result from a regulatory mutation affecting the expression of the genes coding for both proteases.

The initiation of eukaryotic transcription at a specific promoter or set of promoters requires a eukaryotic transcriptional activator which is a polypeptide, but which is not itself part of RNA polymerase. Many transcriptional activators bind to a specific site on the promoter to form a functional promoter necessary for the initiation of transcription of the polypeptide encoding sequence. However, a transcriptional activator may also be incorporated into an initiation complex only in the presence of other polypeptides. Polypeptides with transcriptional activation activity have been described in fungi, and a list of such polypeptides has been published (Dhawale, S. S., and Lane, A. C. 1993. Nucleic Acid Research 21:5537-5546).

It is an object of the present invention to provide improved methods for increasing production of polypeptides in host cells in which the activity of a transcriptional activator involved in the regulation of protease production has been modified.

SUMMARY OF THE INVENTION

A first aspect of the present invention relates to an isolated nucleic acid sequence encoding a transcriptional activator selected from the group consisting of:

(a) a nucleic acid sequence having at least 70% identity with the nucleic acid sequence of SEQ ID NO: 1 or SEQ ID NO: 48;

(b) a nucleic acid sequence encoding a polypeptide having an amino acid sequence which has at least 50% identity with the amino acid sequence of SEQ ID NO: 2 or SEQ ID NO: 49;

(c) a nucleic acid sequence which hybridizes under low stringency conditions with (i) the nucleic acid sequence of SEQ ID NO: 1 or SEQ ID NO: 48, or (ii) its complementary strand, wherein the low stringency conditions are defined by prehybridization and hybridization at 42° C. in 5×SSPE, 0.3% SDS, 200 microg/ml sheared and denatured salmon sperm DNA, and 25% formamide, and wash conditions are defined by 50° C. for 30 minutes in 2×SSC, 0.2% SDS;

(d) an allelic variant of (a), (b), or (c);

(e) a subsequence of (a), (b), (c), or (d), wherein the subsequence encodes a polypeptide fragment which has transcriptional activation activity; and (f) a subsequence of (a), (b) (c), or (d), wherein the subsequence encodes a polypeptide with the amino acid sequence of SEQ ID NO: 3.

The nucleic acid sequence shown in SEQ ID NO: 1 is the *Aspergillus niger* prtT gene encoding the transcriptional factor shown in SEQ ID NO: 2 as described further below and in the Examples.

The nucleic acid sequence shown in SEQ ID NO: 48 is the *Aspergillus oryzae* IFO4177 prtT gene encoding the transcriptional factor shown in SEQ ID NO: 49. The *A. oryzae* prtT gene has a coding region starting in position 795 and ending at position 2931. The prtT gene has 4 introns in positions 1028-1135, 1538-1591, 2018-2066, and 2297-2347, respectively. This is described further below and in the Examples.

In another aspect, the invention also relates to nucleic acid constructs, vectors and host cells comprising the nucleic acid sequences, and to the polypeptides encoded by the nucleic acid sequences. The invention further relates to host cells useful for the production of a polypeptide, in which the production or function of the transcriptional activator has been altered, as well as to methods for producing the polypeptide.

BRIEF DESCRIPTION OF THE FIGURES

FIG. 6 shows the sequence of the insert in the two plasmids containing the PCR fragment of the *A. oryzae* prtT $Zn^{2+}$-finger. ICA217 is the sequence from one of the plasmids and ICA218 is the sequence from the other.

DETAILED DESCRIPTION OF THE INVENTION

Nucleic Acid Sequences Encoding Transcriptional Activators

Figure 1:
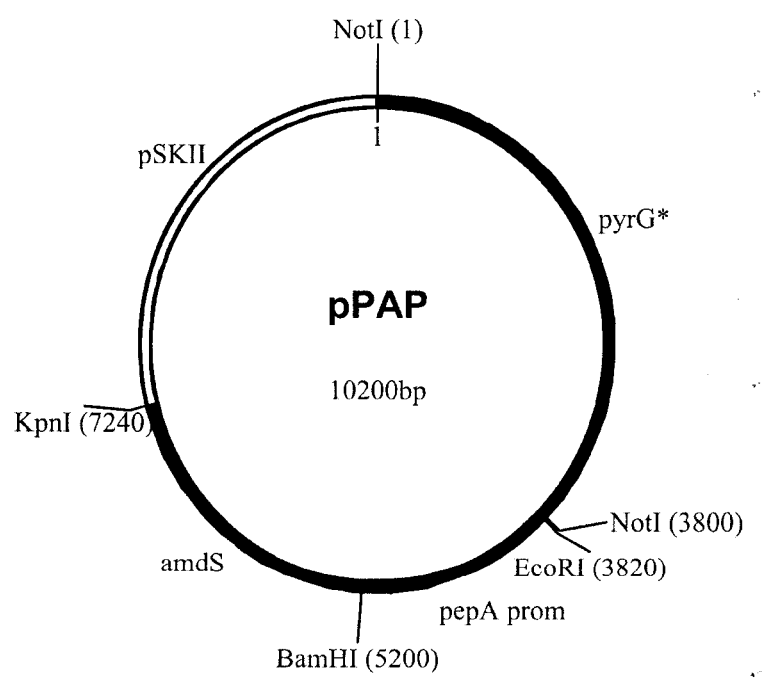
FIG. 1 shows a restriction map of the plasmid pPAP, the construction of which is described in Example 1.

A first aspect of the present invention relates to an isolated nucleic acid sequence encoding a transcriptional activator selected from the group consisting of:

(a) a nucleic acid sequence having at least 70% identity with the nucleic acid sequence of SEQ ID NO: 1 or SEQ ID NO: 48;

(b) a nucleic acid sequence encoding a polypeptide having an amino acid sequence which has at least 50% identity with the amino acid sequence of SEQ ID NO: 2 or SEQ ID NO: 49;

(c) a nucleic acid sequence which hybridizes under low stringency conditions with (i) the nucleic acid sequence of SEQ ID NO: 1 or SEQ ID NO: 48, or (ii) its complementary strand, wherein the low stringency conditions are defined by prehybridization and hybridization at 42° C. in 5×SSPE, 0.3% SDS, 200 micro g/ml sheared and denatured salmon sperm DNA, and 25% formamide, and wash conditions are defined by 50° C. for 30 minutes in 2×SSC, 0.2% SDS;

(d) an allelic variant of (a), (b), or (c);

(e) a subsequence of (a), (b), (c), or (d), wherein the subsequence encodes a polypeptide fragment which has transcriptional activation activity; and (f) a subsequence of (a), (b), (c), or (d), wherein the subsequence encodes a polypeptide with the amino acid sequence of SEQ ID NO: 3.

The term "transcriptional activator" as used herein refers to a polypeptide which has the capability to activate a specific promoter or set of promoters necessary for the initiation of transcription of the polypeptide encoding sequence to which it is linked.

The term "isolated nucleic acid sequence" as used herein refers to a nucleic acid sequence which is essentially free of other nucleic acid sequences, e.g., at least about 20% pure, preferably at least about 40% pure, more preferably at least about 60% pure, even more preferably at least about 80% pure, most preferably at least about 90% pure as determined by agarose electrophoresis. For example, an isolated nucleic acid sequence can be obtained by standard cloning procedures used in genetic engineering to relocate the nucleic acid sequence from its natural location to a different site where it will be reproduced. The cloning procedures may involve excision and isolation of a desired nucleic acid fragment comprising the nucleic acid sequence encoding the polypeptide, insertion of the fragment into a vector molecule, and incorporation of the recombinant vector into a host cell where multiple copies or clones of the nucleic acid sequence will be replicated. The nucleic acid sequence may be of genomic, cDNA, RNA, semisynthetic, synthetic origin, or any combinations thereof.

In a preferred embodiment, the nucleic acid sequence has a degree of identity to the nucleic acid sequence set forth in SEQ ID NO: 1 or SEQ ID NO: 48 of at least about 70%, preferably at least about 80%, more preferably at least about 85%, even more preferably at least about 90%, most preferably at least about 95%, even most preferably at least about 97%, and even more preferred at least 99% identity, which encodes an active polypeptide. For purposes of the present invention, the degree of identity between two nucleic acid sequences is determined by the Clustal method (Higgins, 1989, *CABIOS* 5:151-153) with an identity table, a gap penalty of 10, and a gap length penalty of 10.

In an even more preferred embodiment, the nucleic acid sequence encoding a transcriptional activator has a nucleic acid sequence as set forth in SEQ ID NO: 1 or SEQ ID NO: 48.

Modification of a nucleic acid sequence encoding a polypeptide of the present invention may be necessary for the synthesis of polypeptides substantially similar to the polypeptide. The term "substantially similar" to the polypeptide refers to non-naturally occurring forms of the polypeptide. These polypeptides may differ in some engineered way from the polypeptide isolated from its native source. For example, it may be of interest to synthesize variants of the polypeptide where the variants differ in specific activity, binding specificity and/or affinity, or the like using, e.g., site-directed mutagenesis. The analogous sequence may be constructed on the basis of the nucleic acid sequence presented as the polypeptide encoding part of SEQ ID NO: 1 or SEQ ID NO: 48, e.g., a subsequence thereof, and/or by introduction of nucleotide substitutions which do not give rise to another amino acid sequence of the polypeptide encoded by the nucleic acid sequence, but which corresponds to the codon usage of the host organism intended for production of the enzyme, or by introduction of nucleotide substitutions which may give rise to a different amino acid sequence. For a general description of nucleotide substitution, see, e.g., Ford et al., 1991, *Protein Expression and Purification* 2: 95-107.

In another preferred embodiment, the present invention relates to isolated nucleic acid sequences encoding polypeptides having an amino acid sequence which has a degree of identity to the amino acid sequence set forth in SEQ ID NO: 2 or SEQ ID NO: 49 of at least about 50%, preferably at least about 60%, preferably at least about 70%, more preferably at least about 80%, even more preferably at least about 90%, most preferably at least about 95%, even most preferably at least about 97%, and even more preferred at least 99%, which qualitatively retain the transcriptional activation activity of the polypeptides (hereinafter "homologous polypeptides").

In a preferred embodiment, the homologous polypeptides have an amino acid sequence which differs by five amino acids, preferably by four amino acids, more preferably by three amino acids, even more preferably by two amino acids, and most preferably by one amino acid from the amino acid sequence set forth in SEQ ID NO: 2 or SEQ ID NO: 49. For purposes of the present invention, the degree of identity between two amino acid sequences is determined by the Clustal method (Higgins, 1989, supra) with an identity table, a gap penalty of 10, and a gap length penalty of 10.

Hybridization indicates that by methods of standard Southern blotting procedures, the nucleic acid sequence hybridizes to an oligonucleotide probe corresponding to the polypeptide encoding part of the nucleic acid sequence shown in SEQ ID NO: 1, under low to high stringency conditions (i.e., prehybridization and hybridization at 42° C. in 5×SSPE, 0.3% SDS, 200 micrograms/ml sheared and denatured salmon sperm DNA, and either 25, 35 or 50% formamide for low, medium and high stringencies, respectively). In order to identify a clone or DNA which is homologous with SEQ ID NO: 1 or SEQ ID NO: 48, the hybridization reaction is washed three times for 30 minutes each using 2×SSC, 0.2% SDS preferably at least 50° C., more preferably at least 55° C., more preferably at least 60° C., more preferably at least 65° C., even more preferably at least 70° C., and most preferably at least 75° C.

The nucleic acid sequence of SEQ ID NO: 1 or SEQ ID NO: 48, or a subsequence thereof, as well as the amino acid sequence of SEQ ID NO: 2 or SEQ ID NO: 49, or a partial sequence thereof, or the amino acid sequence of SEQ ID NO: 3, may be used to design an oligonucleotide probe to identify and isolate or clone a homologous gene of any genus or species according to methods well known in the art.

In particular, such probes can be used for hybridization with the genomic or cDNA of the genus or species of interest, following standard Southern blotting procedures, in order to identify and isolate the corresponding gene therein. Such probes can be considerably shorter than the entire sequence, but should be at least 15, preferably at least 25, and more preferably at least 40 nucleotides in length. Longer probes can also be used. Both DNA and RNA probes can be used. The probes are typically labeled for detecting the corresponding gene (for example, with $^{32}P$, $^{3}H$, $^{35}S$, biotin, or avidin). For example, molecules to which a $^{32}P$—, $^{3}H$— or $^{35}S$— labelled oligonucleotide probe hybridizes may be detected by use of X-ray film.

Thus, a genomic, cDNA or combinatorial chemical library prepared from such other organisms may be screened for DNA which hybridizes with the probes described above and which encodes a polypeptide with transcriptional activation activity. Genomic or other DNA from such other organisms may be separated by agarose or polyacrylamide gel electrophoresis, or other separation techniques. DNA from the libraries or the separated DNA may be transferred to and immobilized on nitrocellulose or other suitable carrier material. A clone or DNA which is homologous to SEQ ID NO: 1 or SEQ ID NO: 48 may then be identified following standard Southern blotting procedures.

An allelic variant denotes any of two or more alternative forms of a gene occupying the same chomosomal locus. Allelic variation arises naturally through mutation, and may result in phenotypic polymorphism within populations. Gene mutations can be silent (i.e., no change in the encoded polypeptide) or may encode polypeptides having altered amino acid sequences.

The term "allelic variant of a polypeptide" is a polypeptide encoded by an allelic variant of a gene. In a preferred embodiment, the nucleic acid sequence encoding a transcriptional activator of the present invention is an allelic variant of a nucleic acid sequence selected from the group consisting of nucleic acid sequences: (a) having at least 70% identity with the nucleic acid sequence of SEQ ID NO: 1 or SEQ ID NO: 48, (b) encoding a polypeptide having an amino acid sequence which has at least 50% identity with the amino acid sequence of SEQ ID NO: 2 or SEQ ID NO: 49, (c) which hybridizes under low stringency conditions with the nucleic acid sequence of SEQ ID NO: 1 or SEQ ID NO: 48, or its complementary strand, and (d) encoding a polypeptide having the amino acid sequence of SEQ ID NO: 3.

The present invention also encompasses nucleic acid sequences which differ from SEQ ID NO: 1 or SEQ ID NO: 48 by virtue of the degeneracy of the genetic code. The present invention also relates to subsequences of SEQ ID NO: 1 or SEQ ID NO: 49, wherein a subsequence of SEQ ID NO: 1 is a nucleic acid sequence encompassed by SEQ ID NO: 1 or SEQ ID NO: 48 except that one or more nucleotides from the 5' and/or 3' end have been deleted. Preferably, a subsequence of SEQ ID NO: 1 or SEQ ID NO: 48 encodes a polypeptide fragment which has transcriptional activation activity. In a more preferred embodiment, a subsequence of SEQ ID NO: 1 or SEQ ID NO: 48 contains at least a nucleic acid sequence encoding the polypeptide sequence shown in SEQ ID NO: 3.

The techniques used to isolate or clone a nucleic acid sequence encoding a polypeptide are known in the art and include isolation from genomic DNA, preparation from cDNA, or a combination thereof. The cloning of the nucleic acid sequences of the present invention from such genomic DNA can be effected, e.g., by using methods based on polymerase chain reaction (PCR) or antibody screening of expression libraries to detect cloned DNA fragments with shared structural features. (See, e.g., Innis et al., 1990, *PCR: A Guide to Methods and Application*, Academic Press, New York.) Other nucleic acid amplification procedures such as ligase chain reaction (LCR), ligated activated transcription (LAT) and nucleic acid sequence-based amplification (NASBA) may be used. The nucleic acid sequence may be cloned from a microorganism, or another or related organism and thus, for example, may be an allelic or species variant of the polypeptide encoding region of the nucleic acid sequence.

The transcriptional activators encoded by nucleic acid sequences which hybridize with an oligonucleotide probe which hybridizes with the nucleic acid sequence of SEQ ID NO: 1 or SEQ ID NO: 48, its complementary strand, or allelic variants and subsequences of SEQ ID NO: 1 or SEQ ID NO: 48, or allelic variants and fragments of the transcriptional activators may be obtained from microorganisms of any genus.

In a preferred embodiment, the transcriptional activators may be obtained from a fungal cell. "Fungi" as used herein includes the phyla Ascomycota, Basidiomycota, Chytridiomycota, and Zygomycota (as defined by Hawksworth, et al., in *Ainsworth and Bisby's Dictionary of The Fungi*, 8th edition, 1995, CAB International, University Press, Cambridge, UK) as well as the Oomycota (as cited in Hawksworth et al., 1995, supra, page 171) and all mitosporic fungi (Hawksworth et al., 1995, supra).

In preferred embodiment, the fungal source is a filamentous fungal strain. "Filamentous fungi" include all filamentous forms of the subdivision Eumycota and Oomycota (as defined by Hawksworth et al., 1995, supra). The filamentous fungi are characterized by a mycelia wall composed of chitin, cellulose, glucan, chitosan, mannan, and other complex polysaccharides. Vegetative growth is by hyphal elongation and carbon catabolism is obligately aerobic. Filamentous fungal strains include, but are not limited to, strains of *Acremonium, Aspergillus, Aureobasidium, Cryptococcus, Filibasidium, Fusarium, Humicola, Magnaporthe, Mucor, Myceliophthora, Neocallimastix, Neurospora, Paecilomryces, Penicillium, Piromyces, Schizophyllum, Talaromyces, Thermoascus, Thielavia, Tolypocladium,* and *Trichoderma*.

In a more preferred embodiment, the nucleic acid sequence encoding a transcriptional activator of the present invention is obtained from a strain of *Aspergillus*, such as *A. awamori* or *A. nidulans*. Preferably, the nucleic acid sequence is obtained from a strain of *A. niger* or *A. oryzae*. Even more preferably, the nucleic acid sequence is obtained from an isolate of a strain of *A. niger*, DSM 12298; e.g., the nucleic acid sequence set forth in SEQ ID NO: 1, or from *A. oryzae* IFO 4177, i.e., the nucleic acid sequence set forth in SEQ ID NO: 48.

In another more preferred embodiment, the nucleic acid sequence encoding a transcriptional activator of the present invention is obtained from a strain of *Fusarium*, such as *F. oxysporum*. Preferably, the strain is a strain of *F. venenatum* (*Nirenberg* sp. nov.).

In another preferred embodiment, the nucleic acid sequence encoding a transcriptional activator of the present invention is obtained from a yeast strain, such as a *Candida*, *Kluyveromyces*, *Schizosaccharomyces*, or *Yarrowia* strain. Preferably, the strain is a strain of *Hansenula*, *Pichia*, or *Saccharomyces*.

It will be understood that for the aforementioned species, the invention encompasses both the perfect and imperfect states, and other taxonomic equivalents, e.g., anamorphs, regardless of the species name by which they are known. Those skilled in the art will readily recognize the identity of appropriate equivalents. For example, the polypeptides may be obtained from microorganisms which are taxonomic equivalents of *Aspergillus* as defined by Raper, K. D. and Fennel, D. I. (1965. The Genus *Aspergillus*, The Wilkins Company, Baltimore Md.), regardless of the species name by which they are known. *Aspergilli* are mitosporic fungi characterized by an aspergillum comprised of a conidiospore stipe with no known teleomorphic states terminating in a vesicle, which in turn bears one or two layers of synchronously formed specialized cells, variously referred to as sterigmata or phialides, and asexually formed spores referred to as conidia. Known teleomorphs of *Aspergillus* include *Eurotium*, *Neosartorya*, and *Emericella*. Strains of *Aspergillus* and teleomorphs thereof are readily accessible to the public in a number of culture collections, such as the American Type Culture Collection (ATCC), Deutsche Sammlung von Mikroorganismen und Zellkulturen GmbH (DSM), Centraalbureau Voor Schimmelcultures (CBS), and Agricultural Research Service Patent Culture Collection, Northern Regional Research Center (NRRL).

Furthermore, such transcriptional activators may be identified and obtained from other sources including microorganisms isolated from nature (e.g., soil, composts, water, etc.) using the above-mentioned probes. Techniques for isolating microorganisms from natural habitats are well known in the art. The nucleic acid sequence may then be derived by similarly screening a genomic or cDNA library of another microorganism. Once a nucleic acid sequence encoding a transcriptional activator has been detected with the probe(s), the sequence may be isolated or cloned by utilizing techniques which are known to those of ordinary skill in the art (see, e.g., J. Sambrook, E. F. Fritsch, and T. Maniatus, 1989, *Molecular Cloning, A Laboratory Manual*, 2d edition, Cold Spring Harbor, N.Y.).

In another preferred embodiment, the isolated nucleic acid sequence encodes a polypeptide comprising the amino acid sequence of SEQ ID NO: 2 or SEQ ID NO: 49, or a fragment thereof, which has transcriptional activation activity.

In another preferred embodiment, the isolated nucleic acid sequence encodes a polypeptide comprising the amino acid sequence of SEQ ID NO: 3.

The present invention also relates to isolated nucleic acid sequences encoding a transcriptional activator of the present invention, which, using methods of standard Southern blotting procedures described above (cf., Sambrook, et al., 1989, supra), hybridize under low stringency conditions, more preferably medium stringency conditions, and most preferably high stringency conditions, with an oligonucleotide probe which hybridizes under the same conditions with the nucleic acid sequence set forth in SEQ ID NO: 1 or SEQ ID NO: 48 or its complementary strand, or allelic variants and subsequences of SEQ ID NO: 1 or SEQ ID NO: 48 which encode polypeptide fragments which are transcriptional activators in fungi.

In another more preferred embodiment, the nucleic acid sequence is the nucleic acid sequence encoding a polypeptide, which has DNA binding activity contained in the plasmid pEES which is contained in *Escherichia coli* DSM 12294.

Nucleic Acid Constructs

Another aspect of the present invention relates to nucleic acid constructs comprising a nucleic acid sequence encoding a transcriptional activator of the present invention operably linked to one or more control sequences, which direct the production of the transcriptional activator in a suitable expression host. In a preferred embodiment, the nucleic acid sequence encodes a polypeptide, which is contained in the plasmid pEES harboured in *Escherichia coli* DSM 12294, or the nucleic acid sequence shown in SEQ ID NO: 48 encoding the polypeptide shown in SEQ ID NO: 49.

Expression will be understood to include any step involved in the production of the polypeptide including, but not limited to, transcription, post-transcriptional modification, translation, post-translational modification, and secretion. Manipulation of the nucleic acid sequence encoding a polypeptide prior to its insertion into a vector may be desirable or necessary depending on the expression vector. The techniques for modifying nucleic acid sequences utilizing cloning methods are well known in the art.

"Nucleic acid construct" is defined herein as a nucleic acid molecule, either single- or double-stranded, which is isolated from a naturally occurring gene or which has been modified to contain segments of nucleic acid which are combined and juxtaposed in a manner which would not otherwise exist in nature. The term nucleic acid construct is synonymous with the term expression cassette when the nucleic acid construct contains all the control sequences required for expression of a coding sequence. The term "coding sequence" as defined herein is a sequence, which is transcribed into mRNA and translated into a transcriptional activator of the present invention. The boundaries of the coding sequence are generally determined by the ATG start codon at the 5' end of the mRNA and a transcription terminator sequence located just downstream of the open reading frame at the 3' end of the mRNA. A coding sequence can include, but is not limited to, DNA, cDNA, and recombinant nucleic acid sequences.

The term "control sequences" is defined herein to include all components, which are necessary or advantageous for the expression of a polypeptide. Each control sequence may be native or foreign to the nucleic acid sequence encoding the polypeptide. Such control sequences include, but are not limited to, a leader, a polyadenylation sequence, a propeptide sequence, a promoter, a signal sequence, and a transcription terminator. At a minimum, the control sequences include a promoter, and transcriptional and translational stop signals. The control sequences may be provided with linkers for the purpose of introducing specific restriction sites facilitating ligation of the control sequences with the coding region of the nucleic acid sequence encoding a polypeptide. The term "operably linked" is defined herein as a configuration in which a control sequence is appropriately placed at a position relative to the coding sequence of the DNA sequence such that the control sequence directs the production of a polypeptide.

The control sequence may be an appropriate promoter sequence, a nucleic acid sequence, which is recognized by a host cell for expression of the nucleic acid sequence. The promoter sequence contains transcriptional control sequences, which mediate the expression of the polypeptide. The promoter may be any nucleic acid sequence, which shows transcriptional activity in the cell including mutant, truncated, and hybrid promoters, and may be obtained from genes encoding extracellular or intracellular polypeptides either homologous or heterologous to the cell.

The control sequence may also be a suitable transcription terminator sequence, a sequence recognized by a filamentous fungal cell to terminate transcription. The terminator sequence is operably linked to the 3' terminus of the nucleic acid sequence encoding the polypeptide. Any terminator, which is functional in the cell, may be used in the present invention.

Preferred terminators for filamentous fungal cells are obtained from the genes encoding *Aspergillus oryzae* TAKA amylase, *Aspergillus niger glucoamylase, Aspergillus nidulans* anthranilate synthase, *Aspergillus niger* alpha-glucosidase, and *Fusarium oxysporum* trypsin-like protease.

The control sequence may also be a suitable leader sequence, a nontranslated region of a mRNA which is important for translation by the filamentous fungal cell. The leader sequence is operably linked to the 5' terminus of the nucleic acid sequence encoding the polypeptide. Any leader sequence, which is functional in the cell, may be used in the present invention.

Preferred leaders for filamentous fungal cells are obtained from the genes encoding *Aspergillus oryzae* TAKA amylase and *Aspergillus nidulans* triose phosphate isomerase.

The control sequence may also be a polyadenylation sequence, a sequence which is operably linked to the 3' terminus of the nucleic acid sequence and which, when transcribed, is recognized by the filamentous fungal cell as a signal to add polyadenosine residues to transcribed mRNA. Any polyadenylation sequence, which is functional in the cell, may be used in the present invention.

Preferred polyadenylation sequences for filamentous fungal cells are obtained from the genes encoding *Aspergillus oryzae* TAKA amylase, *Aspergillus niger glucoamylase, Aspergillus nidulans* anthranilate synthase, and *Aspergillus niger* alpha-glucosidase.

The control sequence may also be a signal peptide-coding region, which codes for an amino acid sequence linked to the amino terminus of the polypeptide, which can direct the encoded polypeptide into the cell's secretory pathway. The 5' end of the coding sequence of the nucleic acid sequence may inherently contain a signal peptide-coding region naturally linked in translation reading frame with the segment of the coding region, which encodes the secreted polypeptide.

Alternatively, the 5' end of the coding sequence may contain a signal peptide-coding region, which is foreign to the coding sequence. The foreign signal peptide-coding region may be required where the coding sequence does not normally contain a signal peptide-coding region. Alternatively, the foreign signal peptide-coding region may simply replace the natural signal peptide-coding region in order to obtain enhanced secretion of the polypeptide. The signal peptide-coding region may be obtained from a glucoamylase or an amylase gene from an *Aspergillus* species, or a lipase or proteinase gene from a *Rhizomucor* species. However, any signal peptide-coding region, which directs the expressed polypeptide into the secretory pathway of a filamentous fungal cell, may be used in the present invention.

An effective signal peptide coding region for filamentous fungal cells is the signal peptide coding region obtained from the *Aspergillus oryzae* TAKA amylase gene, *Aspergillus niger* neutral amylase gene, *Rhizomucor miehei* aspartic proteinase gene, or *Humicola lanuginosa* cellulase gene.

The control sequence may also be a propeptide coding region, which codes for an amino acid sequence positioned at the amino terminus of a polypeptide. The resultant polypeptide is known as a proenzyme or propolypeptide (or a zymogen in some cases). A propolypeptide is generally inactive and can be converted to a mature active polypeptide by catalytic or autocatalytic cleavage of the propeptide from the propolypeptide. The propeptide coding region may be obtained from the *Rhizomucor miehei* aspartic proteinase gene, or the *Myceliophthora thermophila* laccase gene (WO 95/33836).

Where both signal peptide and propeptide regions are present at the amino terminus of a polypeptide, the propeptide region is positioned next to the amino terminus of a polypeptide and the signal peptide region is positioned next to the amino terminus of the propeptide region.

Expression Vectors

The present invention also relates to recombinant expression vectors comprising a nucleic acid sequence of the present invention, a promoter, and transcriptional and translational stop signals. The various nucleic acid and control sequences described above may be joined together to produce a recombinant expression vector which may include one or more convenient restriction sites to allow for insertion or substitution of the nucleic acid sequence encoding the polypeptide at such sites. Alternatively, the nucleic acid sequence encoding the polypeptide may be expressed by inserting the sequence or a nucleic acid construct comprising the sequence into an appropriate vector for expression. In creating the expression vector, the coding sequence is located in the vector so that the coding sequence is operably linked with the appropriate control sequences for expression, and possibly secretion.

The recombinant expression vector may be any vector (e.g., a plasmid or virus), which can be conveniently subjected to recombinant DNA procedures and can bring about the expression of the nucleic acid sequence encoding the polypeptide. The choice of the vector will typically depend on the compatibility of the vector with the filamentous fungal cell into which the vector is to be introduced. The vectors may be linear or closed circular plasmids. The vector may be an autonomously replicating vector, i.e., a vector, which exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one which, when introduced into the filamentous fungal cell, is integrated into the genome and replicated together with the chromosome(s) into which it has been integrated. The vector system may be a single vector or plasmid or two or more vectors or plasmids, which together contain the total DNA to be introduced into the genome of the filamentous fungal cell, or a transposon.

The vectors preferably contain one or more selectable markers, which permit easy selection of transformed cells. A selectable marker is a gene the product of which provides for biocide or viral resistance, resistance to heavy metals, prototrophy to auxotrophs, and the like. A selectable marker for use in a filamentous fungal cell may be selected from the group including, but not limited to, amdS (acetamidase), argB (ornithine carbamoyltransferase), bar (phosphinothricin acetyltransferase), hygB (hygromycin phosphotransferase), niaD (nitrate reductase), pyrG (orotidine-5'-phosphate decarboxylase), sC (sulfate adenyltransferase), and trpc (anthranilate synthase), as well as equivalents from other species. Preferred for use in an *Aspergillus* cell are the amdS and pyrG genes of *Aspergillus nidulans* or *Aspergillus oryzae* and the bar gene of *Streptomyces hygroscopicus*.

The vectors preferably contain an element(s) that permits stable integration of the vector into the host cell genome or autonomous replication of the vector in the cell independent of the genome of the cell.

Host Cells

Another aspect of the present invention relates to host cells comprising a nucleic acid construct or an expression vector of the present invention.

The choice of a host cell in the methods of the present invention will to a large extent depend upon the source of the nucleic acid sequence encoding the polypeptide of interest.

The introduction of an expression vector or a nucleic acid construct into a filamentous fungal cell may involve a process consisting of protoplast formation, transformation of the protoplasts, and regeneration of the cell wall in a manner known per se. Suitable procedures for transformation of *Aspergillus* cells are described in EP 238 023 and Yelton et al., 1984, *Proceedings of the National Academy of Sciences USA* 81: 1470-1474. A suitable method of transforming *Fusarium* species is described by Malardier et al., 1989, *Gene* 78: 147-156 or in WO 96/00787.

"Introduction" means introducing a vector comprising the nucleic acid sequence encoding the polypeptide into a filamentous fungal cell so that the vector is maintained as a chromosomal integrant or as a self-replicating extra-chromosomal vector. Integration is generally considered to be an advantage as the nucleic acid sequence is more likely to be stably maintained in the cell. Integration of the vector into the chromosome occurs by homologous recombination, non-homologous recombination, or transposition.

For integration into the host cell genome, the vector may rely on the nucleic acid sequence encoding the polypeptide or any other element of the vector for stable integration of the vector into the genome by homologous or nonhomologous recombination. Alternatively, the vector may contain additional nucleic acid sequences for directing integration by homologous recombination into the genome of the host cell. The additional nucleic acid sequences enable the vector to be integrated into the host cell genome at a precise location(s) in the chromosome(s). To increase the likelihood of integration at a precise location, the integrational elements should preferably contain a sufficient number of nucleic acids, such as 100 to 1,500 base pairs, preferably 400 to 1,500 base pairs, and most preferably 800 to 1,500 base pairs, which are highly homologous with the corresponding target sequence to enhance the probability of homologous recombination. The integrational elements may be any sequence that is homologous with the target sequence in the genome of the host cell. These nucleic acid sequences may be any sequence that is homologous with a target sequence in the genome of the host cell, and, furthermore, may be non-encoding or encoding sequences.

For autonomous replication, the vector may further comprise an origin of replication enabling the vector to replicate autonomously in the host cell.

The procedures used to ligate the elements described above to construct the recombinant expression vectors are well known to one skilled in the art (see, e.g., Sambrook, et al., supra).

In a preferred embodiment, the filamentous fungal host cell is a cell of a species of, but not limited to, *Acremonium, Aspergillus, Fusarium, Humicola, Mucor, Myceliophthora, Neurospora, Penicillium, Thielavia, Tolypocladium,* or *Trichoderma*.

In a more preferred embodiment, the filamentous fungal cell is an *Aspergillus* cell. In another more preferred embodiment, the filamentous fungal cell is an *Acremonium* cell. In another more preferred embodiment, the filamentous fungal cell is a *Fusarium* cell. In another more preferred embodiment, the filamentous fungal cell is a *Humicola* cell. In another more preferred embodiment, the filamentous fungal cell is a *Mucor* cell. In another more preferred embodiment, the filamentous fungal cell is a *Myceliophthora* cell. In another more preferred embodiment, the filamentous fungal cell is a *Neurospora* cell. In another more preferred embodiment, the filamentous fungal cell is a *Penicillium* cell. In another more preferred embodiment, the filamentous fungal cell is a *Thielavia* cell. In another more preferred embodiment, the filamentous fungal cell is a *Tolypocladium* cell. In another more preferred embodiment, the filamentous fungal cell is a *Trichoderma* cell.

In a most preferred embodiment, the filamentous fungal cell is an *Aspergillus awamori, Aspergillus foetidus, Aspergillus japonicus, Aspergillus nidulans, Aspergillus niger* or *Aspergillus oryzae* cell. In another most preferred embodiment, the filamentous fungal cell is a *Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporumr, Fusarium reticulatum, Fusarium roseum, Fusarium sambucinum, Fusarium sarcochroum, Fusarium sulphureum, Fusarium toruloseum, Fusarium trichothecioides,* or *Fusarium venenatum* cell. In an even most preferred embodiment, the filamentous fungal cell is a *Fusarium venenatum* (*Nirenberg* sp. nov.). In another most preferred embodiment, the filamentous fungal cell is a *Humicola insolens* or *Humicola lanuginosa* cell. In another most preferred embodiment, the filamentous fungal cell is a *Mucor miehei* cell. In another most preferred embodiment, the filamentous fungal cell is a *Myceliophthora thermophilum* cell. In another most preferred embodiment, the filamentous fungal cell is a *Neurospora crassa* cell. In another most preferred embodiment, the filamentous fungal cell is a *Penicillium purpurogenum* cell. In another most preferred embodiment, the filamentous fungal cell is a *Thielavia terrestris* cell. In another most preferred embodiment, the *Trichoderma* cell is a *Trichoderma harzianum, Trichoderma koningii, Trichoderma longibrachiatum, Trichoderma reesei* or *Trichoderma viride* cell.

Polypeptides Having Transcriptional Activation Activity

Another aspect of the present invention relates to an isolated polypeptide selected from the group consisting of:

(a) a polypeptide which is encoded in a nucleic acid sequence which hybridizes under low stringency conditions with (i) the nucleic acid sequence of SEQ ID NO: 1 or SEQ ID NO: 48; (ii) its complementary strand, or (iii) a subsequence of SEQ ID NO: 1 or SEQ ID NO: 48 which encodes a polypeptide fragment which has transcriptional activation activity, wherein the low stringency conditions are defined by prehybridization and hybridization at 42° C. in 5×SSPE, 0.3% SDS, 200 micro g/ml sheared and denatured salmon sperm DNA, and 25% formamide, and wash conditions are defined at 50° C. for 30 minutes in 2×SSC, 0.2% SDS;

(b) a polypeptide having an amino acid sequence which has at least 50% identity with the amino acid sequence of SEQ ID NO: 2 or SEQ ID NO: 49;

(c) an allelic variant of (a) or (b);

(d) a fragment of (a), (b), or (c), wherein the fragment has transcriptional activation activity; and (e) a polypeptide comprising the amino acid sequence of SEQ ID NO: 3, or an allelic variant thereof.

The transcriptional activator may be isolated using techniques as described herein. As defined herein, an "isolated" polypeptide is a polypeptide which is essentially free of other polypeptides, e.g., at least about 20% pure, preferably at least about 40% pure, more preferably about 60% pure, even more preferably about 80% pure, most preferably about 90% pure, and even most preferably about 95% pure, as determined by SDS-PAGE.

The present invention also relates to isolated polypeptides having an amino acid sequence which has a degree of identity to the amino acid sequence of SEQ ID NO: 2 or SEQ ID NO: 49 of at least about 50%, preferably at least about 55%, preferably at least about 60%, preferably at least about 65%, preferably at least about 70%, preferably at least about 75%, preferably at least about 80%, more preferably at least about 85%, even more preferably at least about 90%, most preferably at least about 95%, and even most preferably at least about 97%, even more preferred at least 99%, which have transcriptional activation activity.

In more preferred embodiment, the transcriptional activator of the present invention comprises the amino acid sequence of SEQ ID NO: 2 or SEQ ID NO: 49 or a fragment thereof, wherein the fragment retains transcriptional activation activity. In a most preferred embodiment, the polypeptide has the amino acid sequence of SEQ ID NO: 2 or SEQ ID NO: 49. A fragment of SEQ ID NO: 2 or SEQ ID NO: 49 is a polypeptide having one or more amino acids deleted from the amino and/or carboxy terminus of this amino acid sequence. Preferably, a fragment of SEQ ID NO: 2 or SEQ ID NO: 49 contains at least the polypeptide sequence shown in SEQ ID NO: 3.

The amino acid sequences of the homologous polypeptides may differ from the amino acid sequence of SEQ ID NO: 2 or SEQ ID NO: 49 or SEQ ID NO: 3 by an insertion or deletion of one or more amino acid residues and/or the substitution of one or more amino acid residues by different amino acid residues. Preferably, amino acid changes are of a minor nature, that is conservative amino acid substitutions that do not significantly affect the folding and/or activity of the protein; small deletions, typically of one to about 30 amino acids; small amino- or carboxyl-terminal extensions, such as an amino-terminal methionine residue; a small linker peptide of up to about 20-25 residues; or a small extension that facilitates purification by changing net charge or another function, such as a poly-histidine tract, an antigenic epitope or a binding domain.

Examples of conservative substitutions are within the group of basic amino acids (such as arginine, lysine and histidine), acidic amino acids (such as glutamic acid and aspartic acid), polar amino acids (such as glutamine and asparagine), hydrophobic amino acids (such as leucine, isoleucine and valine), aromatic amino acids (such as phenylalanine, tryptophan and tyrosine), and small amino acids (such as glycine, alanine, serine, threonine and methionine). Amino acid substitutions, which do not generally alter the specific activity are known in the art and are described, for example, by H. Neurath and R. L. Hill (1979. *The Proteins*, Academic Press, New York). The most commonly occurring exchanges are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly as well as these in reverse.

In a more preferred embodiment, a transcriptional activator of the present invention is obtained from an *Aspergillus niger* strain, more preferably from *Aspergillus niger* AB4.1 (van Haringsveldt, W., et al., 1987. Mol. Gen. Genet. 206:71-75), and most preferably from *Aspergillus niger* 13PAP2, which has been deposited at DSM as DSM 12298, or a mutant strain thereof, harbouring, e.g., the polypeptide with the amino acid sequence of SEQ ID NO: 2 or SEQ ID NO: 49 or SEQ ID NO: 3.

In another preferred embodiment, the transcriptional activator of the present invention is the polypeptide encoded in the nucleic acid sequence contained in plasmid pEES, which is contained in *Escherichia coli* DSM 12294 or the nucleic acid sequence shown in SEQ ID NO: 48 encoding the polypeptide shown in SEQ ID NO: 49.

The present invention further relates to methods for producing the transcriptional activator of the present invention comprising (a) cultivating a host cell harbouring a nucleic acid construct or an expression vector comprising a nucleic acid sequence encoding the transcriptional activator of the invention under conditions conducive for production of the polypeptide; and (b) recovering the polypeptide.

Host Cells Having Altered Transcriptional Activation Activity

Another aspect of the present invention relates to a host cell which is a mutant of a parent fungal cell useful for the production of a polypeptide in which the parent cell comprises one or more nucleic acid sequences encoding a protease, the transcription of which is activated by a transcriptional activator of the present invention, and the mutant cell produces less of the transcriptional activator and the protease(s) than the parent cell when cultured under the same conditions.

The mutant cell may be constructed using methods well known in the art; for example, by one or more nucleotide insertions or deletions of the gene encoding the transcriptional activator.

In a preferred embodiment the mutant cell is obtained by modification or inactivation of a nucleic acid sequence present in the cell and necessary for expression of the transcriptional activator.

In a more preferred embodiment, the nucleic acid sequence is selected from the group consisting of: (a) a nucleic acid sequence having at least 70% identity with the nucleic acid sequence of SEQ ID NO: 1 or SEQ ID NO: 48; (b) a nucleic acid sequence encoding a polypeptide having an amino acid sequence which has at least 50% identity with the amino acid sequence of SEQ ID NO: 2 or SEQ ID NO: 49; (c) a nucleic acid sequence which hybridizes under low stringency conditions with (i) the nucleic acid sequence of SEQ ID NO: 1 or SEQ ID NO: 48, or (ii) its complementary strand, (d) an allelic variant of (a), (b), or (c); (e) a subsequence of (a), (b), (c), or (d), wherein the subsequence encodes a polypeptide fragment which has transcriptional activation activity; and (f) a subsequence of (a), (b) (c), or (d), wherein the subsequence encodes a polypeptide with the amino acid sequence of SEQ ID NO: 3.

In another preferred embodiment the reduced expression of the transcriptional activator in the mutant cell is obtained by modification or inactivation of a control sequence required for the expression of the transcriptional activator. The term "control sequence" is defined, supra, in the section entitled "Nucleic Acid Constructs." In a more preferred embodiment the control sequence in the mutant cell is a promoter sequence or a functional part thereof, i.e., a part, which is sufficient for affecting expression of the nucleic acid sequence. Other control sequences for possible modification include, but are not limited to, a leader, a polyadenylation sequence, a propeptide sequence, a signal sequence, and a transcription terminator.

Modification or inactivation of the gene may be performed by subjecting the parent cell to mutagenesis and selecting for mutant cells in which the capability to produce a transcriptional activator has been reduced. The mutagenesis, which may be specific or random, may be performed, for example, by use of a suitable physical or chemical mutagenizing agent, by use of a suitable oligonucleotide, or by subjecting the DNA sequence to PCR generated mutagenesis. Furthermore, the mutagenesis may be performed by use of any combination of these mutagenizing agents.

Examples of a physical or chemical mutagenizing agent suitable for the present purpose include ultraviolet (UV) irradiation, hydroxylamine, N-methyl-N'-nitro-N-nitrosoguanidine (MNNG), O-methyl hydroxylamine, nitrous acid, ethyl methane sulphonate (EMS), sodium bisulphite, formic acid, and nucleotide analogues.

When such agents are used, the mutagenesis is typically performed by incubating the parent cell to be mutagenized in the presence of the mutagenizing agent of choice under suitable conditions, and selecting for mutant cells exhibiting reduced expression of the gene.

Modification or inactivation of the gene may be accomplished by introduction, substitution, or removal of one or more nucleotides in the gene's nucleic acid sequence or a regulatory element required for the transcription or translation thereof. For example, nucleotides may be inserted or removed so as to result in the introduction of a stop codon, the removal of the start codon, or a change of the open reading frame. Such modification or inactivation may be accomplished by site-directed mutagenesis or PCR generated mutagenesis in accordance with methods known in the art. Although, in principle, the modification may be performed in vivo, i.e., directly on the fungal cell expressing the gene to be modified, it is preferred that the modification be performed in vitro as exemplified below.

An example of a convenient way to inactivate or reduce expression of the gene by a fungal cell of choice is based on techniques of gene replacement or gene interruption. For example, in the gene interruption method, a nucleic acid sequence corresponding to the endogenous gene or gene fragment of interest is mutagenized in vitro to produce a defective nucleic acid sequence which is then transformed into the parent cell to produce a defective gene. By homologous recombination, the defective nucleic acid sequence replaces the endogenous gene or gene fragment. It may be desirable that the defective gene or gene fragment also encodes a marker, which may be used for selection of transformants in which the nucleic acid sequence has been modified or destroyed.

Alternatively, modification or inactivation of the gene may be performed by established anti-sense techniques using a nucleotide sequence complementary to the nucleic acid sequence of the gene. More specifically, expression of the gene by a filamentous fungal cell may be reduced or eliminated by introducing a nucleotide sequence complementary to the nucleic acid sequence, which may be transcribed in the cell and is capable of hybridizing to the mRNA produced in the cell. Under conditions allowing the complementary antisense nucleotide sequence to hybridize to the mRNA, the amount of protein translated is thus reduced or eliminated.

A nucleic acid sequence complementary to the nucleic acid sequence of SEQ ID NO: 1 or SEQ ID NO: 48 may be obtained from any microbial source. The preferred sources are fungal sources, e.g., yeast and filamentous fungi as described supra. Preferred filamentous fungal sources include, but are not limited to, species of *Acremonium, Aspergillus, Fusarium, Humicola, Myceliophthora, Mucor, Neurospora, Penicillium, Phanerochaete, Thielavia, Tolypocladium,* and *Trichoderma*. Preferred yeast sources include, but are not limited to, species of *Candida, Hansenula, Kluyveromyces, Pichia, Saccharomyces, Schizosaccharomyces,* and *Yarrowia*. Furthermore, the nucleic acid sequence may be native to the filamentous fungal cell.

In another preferred embodiment, the parent cell harbours a gene having a nucleic acid sequence encoding a polypeptide with an amino acid sequence which has at least 50% identity with the amino acid sequence of SEQ ID NO: 2 or SEQ ID NO: 49.

In another preferred embodiment, the parent cell harbours a gene having a nucleic acid sequence with at least 70% identity with the nucleic acid sequence of SEQ ID NO: 1 or SEQ ID NO: 48.

In another preferred embodiment, the mutant cell harbours a nucleic acid sequence, which has been modified or inactivated by any of the methods described above and produces less of a protease or a combination of proteases than the parent cell when cultured under identical conditions. The mutant cell produces preferably at least about 25% less, more preferably at least about 50% less, even more preferably at least about 75% less, and even more preferably at least about 95% less of a protease or a combination of proteases than the parent cell when cultured under identical conditions.

In an even more preferred embodiment, the mutant cell produces essentially undetectable amounts of a protease or combination of proteases than the parent cell when cultured under identical conditions.

The protease(s) may be assayed using known methods. In one such method, an aliquot of a 48 hour culture media is incubated with $^3$H-labelled sperm whale myoglobin at pH 4.0 and the radioactivity in the TCA-soluble fraction is measured (van Noort, J. M., et al., 1991. Anal. Biochem 198:385-390). Other methods have been described for identifying, e.g., aspartic proteinase A. of *A. niger* (Takahashi, K., 1991. Meth. in Enzymol. 248:146-155), endopeptidases (Morihara, K., 1995. Meth. in Enzymol. 248:242-253), carboxypeptidases (Reminton, J., and Breddam, K., 1994. Meth. in Enzymol. 244:231-248), dipeptidyl peptidase (Ikehara, Y., et al., 244: 215-227), and aminopeptidases (Little, G., et al., 1976. Meth. in Enzymol. 45:495-503).

In another preferred embodiment, the mutant cell harbours at least one copy of a nucleic acid sequence encoding a polypeptide of interest.

Another aspect of the present invention relates to a host cell useful for the production of a polypeptide wherein the host cell is a mutant of a parent fungal cell in which the mutant (a) produces more of the transcriptional activator of the present invention as compared to the parent cell when cultured under the same conditions; and (b) comprises a DNA sequence encoding the polypeptide, the transcription of which is activated by the transcriptional activator.

In a preferred embodiment, the host cell produces more of the transcriptional activator than the parent cell when cultured under the same conditions by introducing into the parent cell one or more copies of (i) a nucleic acid sequence encoding a transcriptional activator, (ii) a nucleic acid construct comprising a nucleic acid sequence encoding a transcriptional activator, or (iii) an expression vector as defined above in the section "Expression Vectors".

The nucleic acid construct comprising a nucleic acid sequence encoding a transcriptional activator of the present invention may also comprise one or more nucleic acid sequences which encode one or more factors that are advantageous for directing the expression of the polypeptide, e.g., a transcriptional activator (e.g., a trans-acting factor), a chaperone, and a processing protease. Any factor that is functional in the filamentous fungal cell of choice may be used in the present invention. The nucleic acids encoding one or more of these factors are not necessarily in tandem with the nucleic acid sequence encoding the polypeptide.

An activator is a protein, which activates transcription of a nucleic acid sequence encoding a polypeptide (Kudla et al., 1990, *EMBO Journal* 9: 1355-1364; Jarai and Buxton, 1994, *Current Genetics* 26: 2238-244; Verdier, 1990, *Yeast* 6: 271-297). The nucleic acid sequence encoding an activator may be obtained from the genes encoding *Saccharomyces cerevisiae* heme activator protein 1 (hap1), *Saccharomyces cerevisiae* galactose metabolizing protein 4 (gal4), *Aspergillus nidulans* ammonia regulation protein (areA), and *Aspergillus oryzae* alpha-amylase activator (amyR). For further examples, see Verdier, 1990, supra and MacKenzie et al., 1993, *Journal of General Microbiology* 139: 2295-2307.

A chaperone is a protein which assists another polypeptide in folding properly (Hartl et al., 1994, TIBS 19: 20-25; Bergeron et al., 1994, TIBS 19: 124-128; Demolder et al., 1994, *Journal of Biotechnology* 32: 179-189; Craig, 1993, *Science* 260: 1902-1903; Gething and Sambrook, 1992, *Nature* 355: 33-45; Puig and Gilbert, 1994, *Journal of Biological Chemistry* 269: 7764-7771; Wang and Tsou, 1993, *The FASEB Journal* 7: 1515-11157; Robinson et al., 1994, *Bio/Technology* 1: 381-384; Jacobs et al., 1993, *Molecular Microbiology* 8: 957-966). The nucleic acid sequence encoding a chaperone may be obtained from the genes encoding *Aspergillus oryzae* protein disulphide isomerase or *Saccharomyces cerevisiae* calnexin, *Saccharomyces cerevisiae* BiP/GRP78, and *Saccharomyces cerevisiae* Hsp70. For further examples, see Gething and Sambrook, 1992, supra, and Hartl et al., 1994, supra.

A processing protease is a protease that cleaves a propeptide to generate a mature biochemically active polypeptide (Enderlin and Ogrydziak, 1994, Yeast 10: 67-79; Fuller et al., 1989, *Proceedings of the National Academy of Sciences USA* 86: 1434-1438; Julius et al., 1984, *Cell* 37: 1075-1089; Julius et al., 1983, *Cell* 32: 839-852; U.S. Pat. No. 5,702,934). The nucleic acid sequence encoding a processing protease may be obtained from the genes encoding *Saccharomyces cerevisiae* dipeptidylaminopeptidase, *Saccharomyces cerevisiae* Kex2, *Yarrowia lipolytica* dibasic processing endoprotease (xpr6), and *Fusarium oxysporum* metalloprotease (p45 gene).

In a more preferred embodiment, the nucleic acid sequence encoding the transcriptional activator is operably linked to a promoter, or a functional part thereof, which is stronger than the corresponding promoter of the parent cell. In an even more preferred embodiment, the promoter, or a functional part thereof, mediates the expression of a gene encoding an extracellular protease, such as the *Aspergillus oryzae* alkaline protease, *A. oryzae* neutral metalloprotease, *A. niger* aspergillopepsin protease, *Fusarium oxysporum* trypsin-like protease or *F. venenatum* trypsin.

The present invention also relates to a host cell useful for the production of a polypeptide wherein the host cell is a mutant of a parent fungal cell in which the mutant comprises
a) a modification or inactivation of a transcriptional activator of the present invention, or a regulatory sequence thereof, and
b) (i) an inducible promoter operably linked to a nucleic acid sequence encoding a transcriptional activator of the present invention, and (ii) a promoter sequence to which the transcriptional activator can bind, operably linked to a nucleic acid sequence encoding the polypeptide, wherein (i) and (ii) can be introduced simultaneously or sequentially.

The inactive form of the transcriptional activator in (a) above is obtained by inactivation or modification of a nucleic acid sequence present in the cell and necessary for the expression of the native transcriptional activator according to any of the methods as disclosed supra. In a preferred embodiment the inactivation or modification is obtained by methods, which include, but are not limited to, one or more nucleotide insertions, deletions or substitutions, specific or random mutagenesis, gene replacement or gene interruption, and antisense techniques using a nucleotide sequence complementary to the nucleic acid sequence of the transcriptional activator. In another preferred embodiment, the inactive form of the native transcriptional activator is obtained by inactivation or modification of a control sequence required for the expression of the transcriptional activator.

In another preferred embodiment, the nucleic acid sequence encoding the native transcriptional activator has the sequence set forth in SEQ ID NO: 1 or SEQ ID NO: 48. In another preferred embodiment, the transcriptional activator comprises the polypeptide having the amino acid sequence in SEQ ID NO: 3.

The inducible promoter sequence in (b) above may be any promoter sequence, or a functional part thereof, wherein the transcription initiation activity of the promoter can be induced according to the fermentation conditions. Preferably, the induction is mediated by a carbon or nitrogen catabolite. In a preferred embodiment, the promoter is the amdS promoter of *Aspergillus nidulans* or *A. oryzae*, the niaD promoter of *A. nidulans*, *A. oryzae* or *A. niger*, the niiA promoter of *Aspergillus* species, the alkaline phosphatase promoter of *Aspergillus* sp., the acid phosphatase promoter of *Aspergillus* sp., or the alcA promoter of *A. niger*.

In another preferred embodiment, the host cell further comprises a promoter sequence, wherein the promoter sequence can be activated by the transcriptional activator and is operably linked to the nucleic acid sequence encoding the polypeptide.

The promoter sequence activated by the transcriptional activator of the present invention may be any promoter sequence, or a functional part thereof, selected from the group which includes but is not limited to promoters obtained from the genes encoding *Aspergillus oryzae* TAKA amylase, *Rhizomucor miehei* aspartic proteinase, *Aspergillus niger* neutral alpha-amylase, *Aspergillus niger* acid stable alpha-amylase, *Aspergillus niger* or *Aspergillus awamori* glucoamylase (glaA), *Rhizomucor miehei* lipase, *Aspergillus oryzae* alkaline protease, *Aspergillus oryzae* triose phosphate isomerase, *Aspergillus nidulans* acetamidase, the NA2-tpi promoter (a hybrid of the promoters from the genes encoding *Aspergillus niger* neutral alpha-amylase and *Aspergillus oryzae* triose phosphate isomerase), and mutant, truncated, and hybrid promoters thereof. Particularly preferred promoters for use in filamentous fungal cells are a promoter, or a functional part thereof, from a protease gene; e.g., from the *Fusarium oxysporum* trypsin-like protease gene (U.S. Pat. No. 4,288, 627), *Aspergillus oryzae* alkaline protease gene (alp), *Aspergillus niger* pacA gene, *Aspergillus oryzae* alkaline protease gene, *A. oryzae* neutral metalloprotease gene, *A. niger* aspergillopepsin protease gene, or *F. venenatum* trypsin gene.

In another preferred embodiment, the host cell harbours at least one copy of a nucleic acid sequence encoding a polypeptide.

In another preferred embodiment, the host cell, which expresses the transcriptional activator of the present invention produces less of one or more native proteases than the parent cell when cultured under identical conditions. The protease(s) may be assayed using any of the methods described above. In a more preferred embodiment, an aliquot from a 48-hour culture media is incubated with $^3$H-labelled sperm whale myoglobin at pH 4.0 and the radioactivity in the TCA-soluble fraction is measured (van Noort, J. M., et al., supra).

The nucleic acid constructs described herein may be introduced into a parent fungal cell according to any of the methods as described supra in the section, "Host Cells" to obtain a host cell useful for the production of a polypeptide. In a preferred embodiment the nucleic acid construct is integrated into the chromosome of the cell. In another preferred embodiment the nucleic acid construct is maintained as a self-replicating extra-chromosomal vector.

It will be understood that the methods of the present invention are not limited to a particular order for obtaining the mutant fungal cell. The modification of the second nucleic acid sequence may be introduced into the parent cell at any step in the construction of the cell for the production of a polypeptide.

Producing a Polypeptide

Another aspect of the present invention relates to methods of producing a polypeptide in a host cell of the present invention, comprising: (a) cultivating the host cell which harbours a gene encoding the polypeptide in a nutrient medium suitable for production of the polypeptide; and (b) recovering the polypeptide from the nutrient medium of the host cell.

In one embodiment, the host cell which is a mutant of a parent fungal cell in which the parent cell comprises one or more nucleic acid sequences encoding a protease, the transcription of which is activated by a transcriptional activator of the present invention, and the mutant cell produces less of the transcriptional activator and the protease(s) than the parent cell when cultured under the same conditions.

In another embodiment, the host cell is a mutant of a parent fungal cell in which the mutant (a) produces more of the transcriptional activator of the present invention as compared to the parent cell when cultured under the same conditions; and (b) comprises a DNA sequence encoding the polypeptide, the transcription of which is activated by the transcriptional activator.

In another embodiment, the host cell is a mutant of a parent fungal cell in which the mutant comprises (a) a modification or inactivation of a transcriptional activator of the present invention or a regulatory sequence thereof, and (b) an inducible promoter operably linked to a nucleic acid sequence encoding a transcriptional activator of the present invention and a promoter sequence to which the transcriptional activator can bind, operably linked to a nucleic acid sequence encoding the polypeptide, wherein (i) and (ii) can be introduced simultaneously or sequentially.

The host cells of the present invention are cultivated in a nutrient medium suitable for production of the polypeptide of interest using methods known in the art. For example, the cells may be cultivated by shake flask cultivation, small-scale or large-scale fermentation (including continuous, batch, fed-batch, or solid state fermentations) in laboratory or industrial fermentors performed in a suitable medium and under conditions allowing the polypeptide to be expressed and/or isolated. The cultivation takes place in a suitable nutrient medium comprising carbon and nitrogen sources and inorganic salts, using procedures known in the art (see, e.g., Bennett, J. W. and LaSure, L., eds., *More Gene Manipulations in Fungi*, Academic Press, CA, 1991). Suitable media are available from commercial suppliers or may be prepared using published compositions (e.g., in catalogues of the American Type Culture Collection). If the polypeptide is secreted into the nutrient medium, the polypeptide can be recovered directly from the medium. If the polypeptide is not secreted, it is recovered from cell lysates.

The resulting polypeptide may be isolated by methods known in the art. For example, the polypeptide may be isolated from the nutrient medium by conventional procedures including, but not limited to, centrifugation, filtration, extraction, spray drying, evaporation, or precipitation. The isolated polypeptide may then be further purified by a variety of procedures known in the art including, but not limited to, chromatography (e.g., ion exchange, affinity, hydrophobic, chromatofocusing, and size exclusion), electrophoretic procedures (e.g., preparative isoelectric focusing, differential solubility (e.g., ammonium sulfate precipitation), or extraction (see, e.g., *Protein Purification*, J.-C. Janson and Lars Ryden, editors, VCH Publishers, New York, 1989).

The polypeptide may be detected using methods known in the art that are specific for the polypeptide. These detection methods may include use of specific antibodies, formation of an enzyme product, disappearance of an enzyme substrate, or SDS-PAGE. For example, an enzyme assay may be used to determine the activity of the polypeptide. Procedures for determining enzyme activity are known in the art for many enzymes.

In the methods of the present invention, the host cell produces at least about 20% more, preferably at least about 50% more, more preferably at least about 100% more, even more preferably at least about 200% more, and most preferably at least about 300% more of the polypeptide than a corresponding parent cell when cultivated under the same conditions.

The polypeptide may be any polypeptide whether native or heterologous to the mutant filamentous fungal cell. The term "heterologous polypeptide" is defined herein as a polypeptide, which is not produced by a cell. The term "polypeptide" is not meant herein to refer to a specific length of the encoded produce and therefore encompasses peptides, oligopeptides and proteins. The polypeptide may also be a recombinant polypeptide, which is a polypeptide native to a cell, which is encoded by a nucleic acid sequence, which comprises one or more control sequences foreign to the nucleic acid sequence, which are involved in the production of the polypeptide. The polypeptide may be a wild-type polypeptide or a variant thereof. The polypeptide may also be a hybrid polypeptide, which contains a combination of partial or complete polypeptide sequences obtained from at least two different polypeptides where one or more of the polypeptides may be heterologous to the cell. Polypeptides further include naturally occurring allelic and engineered variations of the above-mentioned polypeptides.

In a preferred embodiment, the polypeptide is an antibody or portions thereof, an antigen, a clotting factor, an enzyme, a hormone or a hormone variant, a receptor or portions thereof, a regulatory protein, a structural protein, a reporter, or a transport protein.

In a more preferred embodiment, the enzyme is an oxidoreductase, transferase, hydrolase, lyase, isomerase, or ligase.

In an even more preferred embodiment, the enzyme is an aminopeptidase, amylase, carbohydrase, carboxypeptidase, catalase, cellulase, chitinase, cutinase, deoxyribonuclease, dextranase, esterase, alpha-galactosidase, beta-galactosidase, glucoamylase, alpha-glucosidase, beta-glucosidase, haloperoxidase, invertase, laccase, lipase, mannosidase, mutanase, oxidase, pectinolytic enzyme, peroxidase, phytase, polyphenoloxidase, proteolytic enzyme, ribonuclease, transglutaminase, or xylanase.

In another even more preferred embodiment, the polypeptide is human insulin or an analog thereof, human growth hormone, erythropoietin, or insulinotropin.

The nucleic acid sequence encoding a heterologous polypeptide may be obtained from any prokaryotic, eukaryotic, or other source. For purposes of the present invention, the term "obtained from" as used herein in connection with a given source shall mean that the polypeptide is produced by the source or by a cell in which a gene from the source has been inserted.

In the methods of the present invention, the mutant filamentous fungal cells may also be used for the recombinant production of polypeptides, which are native to the cell. The native polypeptides may be recombinantly produced by, e.g., placing a gene encoding the polypeptide under the control of a different promoter to enhance expression of the polypeptide, to expedite export of a native polypeptide of interest outside the cell by use of a signal sequence, and to increase the copy number of a gene encoding the polypeptide normally produced by the cell. The present invention also encompasses, within the scope of the term "heterologous polypeptide", such recombinant production of polypeptides native to the cell, to the extent that such expression involves the use of genetic elements not native to the cell, or use of native elements which have been manipulated to function in a manner that do not normally occur in the filamentous fungal cell. The techniques used to isolate or clone a nucleic acid sequence encoding a heterologous polypeptide are known in the art and include isolation from genomic DNA, preparation from cDNA, or a combination thereof. The cloning of the nucleic acid sequences from such genomic DNA can be effected, e.g., by using the well known polymerase chain reaction (PCR). See, for example, Innis et al., 1990, *PCR Protocols: A Guide to Methods and Application*, Academic Press, New York. The cloning procedures may involve excision and isolation of a desired nucleic acid fragment comprising the nucleic acid sequence encoding the polypeptide, insertion of the fragment into a vector molecule, and incorporation of the recombinant vector into the mutant fungal cell where multiple copies or clones of the nucleic acid sequence will be replicated. The nucleic acid sequence may be of genomic, cDNA, RNA, semisynthetic, synthetic origin, or any combinations thereof.

In the methods of the present invention, heterologous polypeptides may also include fused or hybrid polypeptides in which another polypeptide is fused at the N-terminus or the C-terminus of the polypeptide or fragment thereof. A fused polypeptide is produced by fusing a nucleic acid sequence (or a portion thereof) encoding one polypeptide to a nucleic acid sequence (or a portion thereof) encoding another polypeptide. Techniques for producing fusion polypeptides are known in the art, and include, ligating the coding sequences encoding the polypeptides so that they are in frame and expression of the fused polypeptide is under control of the same promoter(s) and terminator. The hybrid polypeptides may comprise a combination of partial or complete polypeptide sequences obtained from at least two different polypeptides wherein one or more may be heterologous to the mutant fungal cell. An isolated nucleic acid sequence encoding a heterologous polypeptide of interest may be manipulated in a variety of ways to provide for expression of the polypeptide. Expression will be understood to include any step involved in the production of the polypeptide including, but not limited to, transcription, post-transcriptional modification, translation, post-translational modification, and secretion. Manipulation of the nucleic acid sequence encoding a polypeptide prior to its insertion into a vector may be desirable or necessary depending on the expression vector. The techniques for modifying nucleic acid sequences utilizing cloning methods are well known in the art.

The present invention is further described by the following examples, which should not be construed as limiting the scope of the invention.

EXAMPLES

Materials

Chemicals used as buffers and substrates were commercial products of at least reagent grade.

Strains

AB4.1: a strain of *Aspergillus niger* which is a cspA1 pyrG1 derivative of strain ATTC 9029 (van Hartingsveldt, W., et al., 1987. Mol. Gen. Genet. 206:71-75; Bos, C. J., et al., Curr. Genet. 14:437-443)

AB1.13: a protease deficient strain of *Aspergillus niger* derived from UV mutagenesis of AB4.1 (Mattern, I. E., et al., 1992. Mol. Gen. Genet. 234:332-336)

13PAP2: an AB1.13 derivative containing multiple copies of the *A. nidulans* amdS gene (Corrick, R. A., et al, 1987. Gene 53: 63-71) under control of the pepA promoter of *A. niger* (Jarai G. and Buxton F. 1994. Curr Genet. 26:238-244). The strain has a protease deficient phenotype and is unable to grow on medium containing acetamide as the sole nitrogen source. Strain 13PAP2 has been deposited at DSM under the name DSM No. 12298.

4PAP6: an AB4.1 derivative containing multiple copies of the of *A. nidulans* amdS gene under control of the pepA promoter of *A. niger*. The strain does not have a protease deficient phenotype and is able to grow on medium containing acetamide as the sole nitrogen source.

N402: a strain of *Aspergillus niger*, deposited at the ATCC (Manassas Va., USA) as ATCC Number: 64974

MC1046: a strain of *E. coli*, deposited at the ATCC as ATCC Number: 35467

*A. oryzae* IFO4177: available from Institute for Fermentation, Osaka; 17-25 Juso Hammachi 2-Chome Yodogawa-Ku, Osaka, Japan.

HowB101: described in WO 97/35956.

Figure 7:
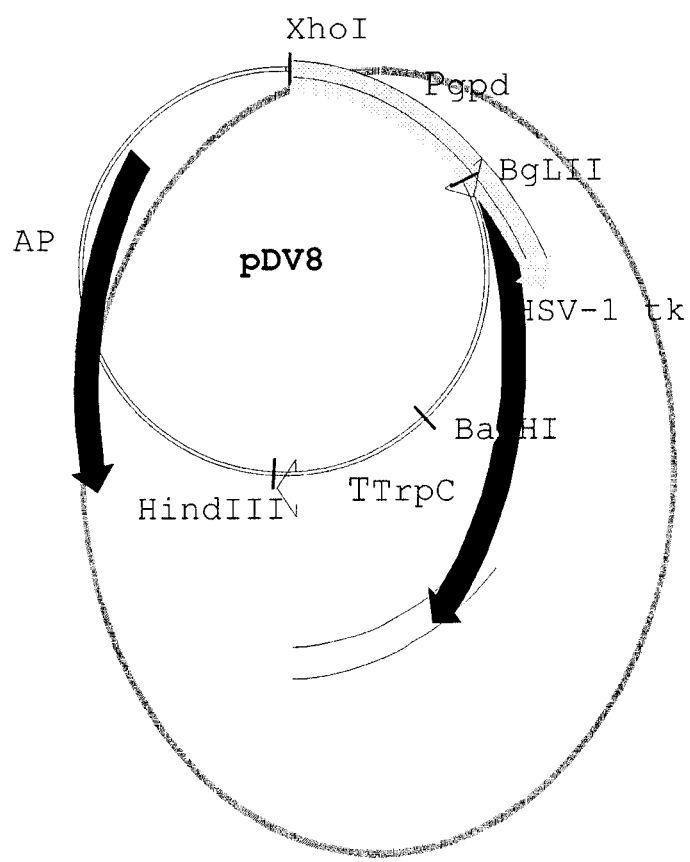
FIG. 7 shows plasmid pDV8 a pSP65 (Promega™) based plasmid containing the HSV-tk gene on a 1.2 kb BglII/BamHI fragment inserted between a 1.0 kb XhoI/BglII fragment of the *A. nidulans* gpd promoter and a 0.8 kb BamHI/HindIII fragment containing the *A. nidulans* trpc transcriptional terminator.
Figure 8:
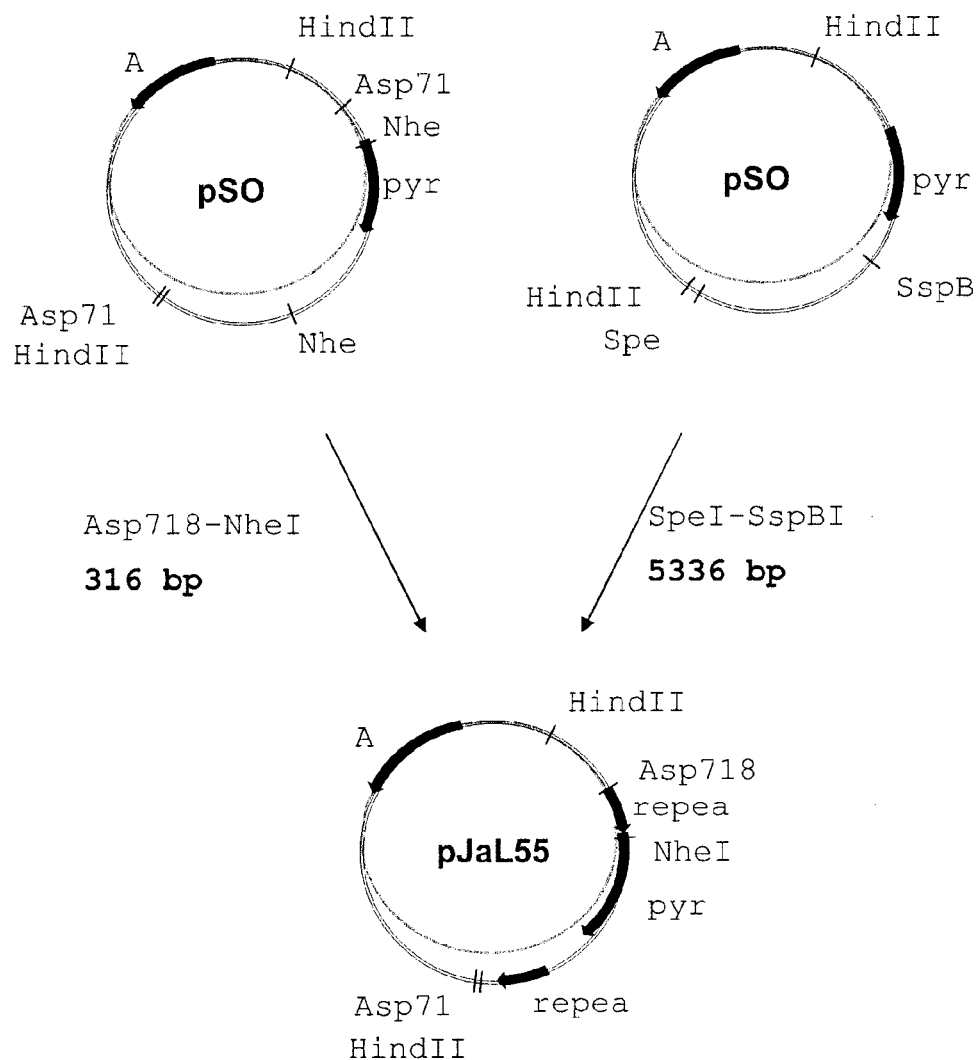
FIG. 8 shows the construction of pJaL554 described in Example 8.

Plasmids pPAP: constructed as described below in Example 1 and shown in FIG. 1 pAopyrGcosArp1: constructed as described below in Example 1 and shown in FIG. 2 pEES1: constructed as described below in Example 1 and shown in FIG. 3 p3SR2: contains the *A. nidulans* amdS gene as described by C. M. Corrick, A. P. Twomey, and M. J. Hynes (1987. Gene 53: 63-71)

pABPYRG*-Not: contains an inactivated pyrG gene as described by Verdoes, J. C., et al. (1994. Gene 145: 179-187)

pHelp1: contains the pyrG gene from *A. oryzae* as a selective marker and the AMAL sequences which enable autonomous replication in *A. niger*, cloned into the *E. coli* vector pIC20R, as described by Gems, D., et al. (1991. Gene 98: 61-67)

pAnscos1: contains two cos sites as described by Osiewacz, H. D. (1994. Curr. Genet. 26: 87-90)

pAO4-2: contains the *A. oryzae* pyrG gene as described by De Ruiter-Jacobs, Y. M. J. T., et al. (1989. Curr. Genet. 16: 159-163)

pAO4-13: contains the *A. oryzae* pyrG gene as described by De Ruiter-Jacobs, Y. M. J. T., et al. (1989. Curr. Genet. 16:159-163)

pUC19: as described by Yanisch-Perron, C., Vieira, J. and Messig, J. (1985, Gene 33:103-119)

pDV8: described in Example 8 and shown in FIG. 7.

pJaL554: described in Example 8 and shown in FIG. 8

Deposit of Biological Materials

The following biological material has been deposited under the terms of the Budapest Treaty with the Deutsche Sammlung von Microorganismen und Zellkulturen GmbH, Mascheroder Weg 1b, D-38124 Braunschweig, Germany and given the following accession number:

| Deposit | Accession Number | Date of Deposit |
|---|---|---|
| *Escherichia coli*, pEES | DSM 12294 | Jul. 14, 1998 |
| *Aspergillus niger* 13PAP2 | DSM 12298 | Jul. 14, 1998 |

The strain has been deposited under conditions that assure that access to the culture will be available during the pendency of this patent application. The deposit represents a substantially pure culture of the deposited strain. The deposit is available as required by foreign patent laws in countries wherein counterparts of the subject application, or its progeny are filed. However, it should be understood that the availability of a deposit does not constitute a license to practice the subject invention in derogation of patent rights granted by governmental action.

Example 1

Cloning of the *A. niger* prtT Transcriptional Activator

The prtT gene was cloned from 13PAP2, an *A. niger* mutant strain which is unable to express the amdS gene regulated by the pepA protease gene promoter and has a protease deficient phenotype (prt⁻).

Construction of the *A. niger* 13PAP2 Reporter Strain

The plasmid pPA1 was constructed by ligation of the following three fragments:

1) the *E. coli* vector pBlueScript II SK (Stratagene Cloning Systems, La Jolla Calif., USA) digested with EcoRI and KpnI;

2) a 1.4 kb EcoRI/BamHI restriction fragment containing the 1.2 kb promoter region of the pepA gene linked to about 130 bp of the amdS coding sequence from the start codon to an internal BamHI site, amplified by PCR; and 3) a 2.1 kb BamHI/KpnI fragment from p3SR2 which contains most of the *A. nidulans* amdS gene Fragment 2 was constructed in two steps. In a first step genomic DNA from *A. niger* N402 prepared from protoplasts as described below in the section "Construction of the Cosmid Library" was used as the template, and the two oligonucleotides shown below, pepApr and pepA/amdS, were used as primers:

```
PepApr:
                                     (SEQ ID NO: 6)
CGG AAT TCG CAT GCT GGA GGT GCT TCT AA pepA/amdS:
                                     (SEQ ID NO: 7)
TTC CCA GGA TTG AGG CAT TTT GAC CAC GAG AAT
```

The 1200 bp PCR product obtained from this reaction was then used as a primer in a second PCR reaction together with the oligonucleotide MBL1213 shown below, and plasmid p3SR2 as the template. MBL1213: TAA CTT CCA CCG AGG TC (SEQ ID NO: 8)

The product obtained by ligation of the three fragments described above was subsequently transfected into *E. coli* DH5α.

In the final construction procedure, pPA1 was digested with NotI and ligated to a 3.8 kb NotI fragment from pAB-PYRG*-Not, resulting in plasmid pPAP which is shown in FIG. 1. pPAP was transformed into *A. niger* AB 1.13, and a transformant with pPAP integrated into the pyrG locus in multicopy was isolated. A spontaneous 5 fluorotic acid (FOA) resistant, uridine-requiring mutant of this transformant that could be complemented with the pyrG gene was named 13PAP2.

Construction of pAopyrGcosArp1

Figure 2:
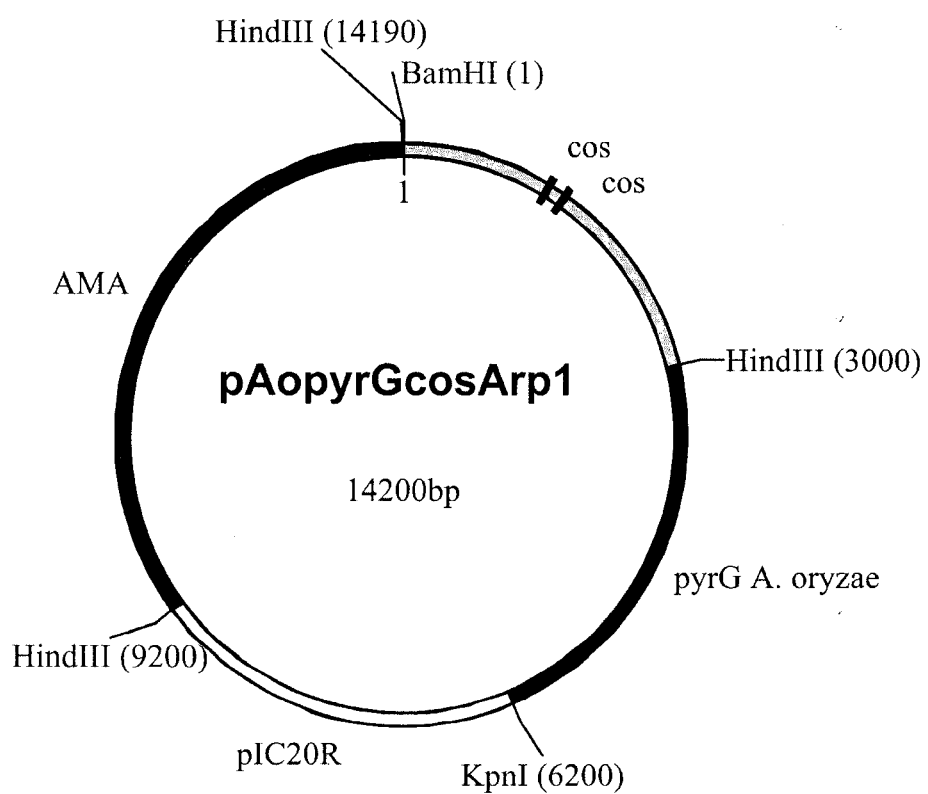
FIG. 2 shows a restriction map of the plasmid pAopyrG-cosArp1, the construction of which is described in Example 1.
Figure 3:
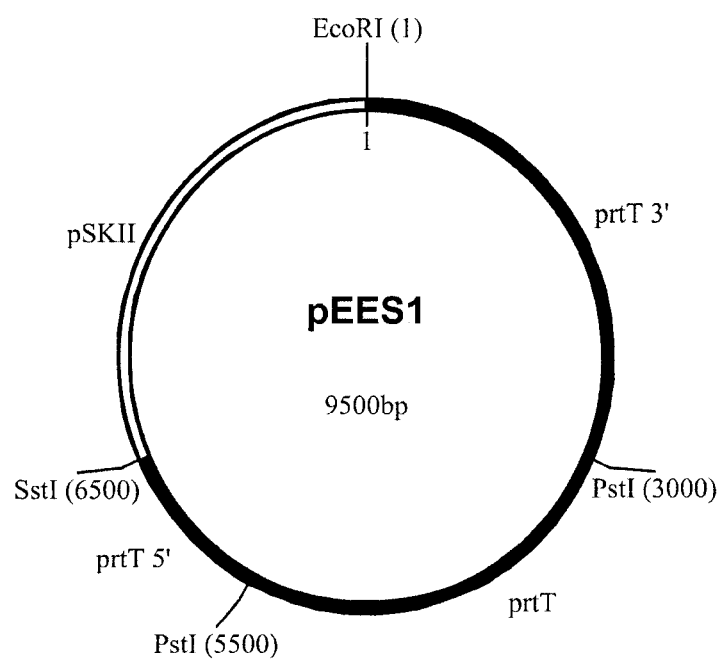
FIG. 3 shows a restriction map of the plasmid pEES1, the construction of which is described in Example 1.

The plasmid pAopyrGcosArp1 was constructed by ligation and subsequent transfection into *E. coli* DH5☐ of the following three fragments:

1) the *E. coli* vector pHelp1 cut with Acc65I and BamHI 2) a 3.0 kb BamHI/HindIII fragment from pAnscos1 containing two cos sites 3) a 3.2 kb Acc65I/HindIII fragment from pAO4-2 containing the *A. oryzae* pyrG gene The resulting plasmid, pAopyrGcosArp1, is self-replicating in *Aspergilli* and can be selected for by growth on medium lacking uridine. pAopyrGcosArp1 is depicted in FIG. 2.

Construction of the Cosmid Library.

A cosmid library of *Aspergillus niger* was constructed using the "SuperCos1 cosmid vector kit" (Stratagene Cloning Systems, La Jolla Calif., USA) according to the supplier's instructions.

Genomic DNA from *A. niger* N402 was prepared from protoplasts made by standard procedures.

After isolation the protoplasts were pelleted by centrifugation at 2000 rpm for 10 minutes in a Beckman GS-6R; the pellet was then suspended in a buffer containing 22.5 mM tri-isonaphtalene sulphonic acid, 275 mM para-aminosalicylic acid, 0.2 M Tris-HCl (pH 8.5), 0.25 M NaCl and 50 mM EDTA immediately followed by addition of 1 volume of phenol/chloroform (1:1). After careful mixing and centrifugation at 3000 rpm for 20 minutes the aqueous phase was decanted and DNA was precipitated using standard procedures.

The size of the genomic DNA was analysed by electrophoresis on a 0.3% agarose gel run for 20 hours at 30 volts at 4° C. The ethidium bromide stained gel showed that the recovered DNA ranged in size from 50 to greater than 100 kb. The DNA was partially digested using MboI. The size of the digested DNA was 30 to 50 kb as determined by the same type of gel analysis as above. The pAopyrGcosArp1 vector, purified using a kit from QIAGEN (Venlo, The Netherlands) following the manufacturer's instructions, was digested with BamHI, dephosphorylated and gel purified. Ligation and packaging were performed following standard procedures.

After titration of the library, all of the packaging mix from a single ligation and packaging was transfected into the host cell, MC1046, and plated on 50 µg/ml ampicillin LB plates. Approximately 40,000 colonies were obtained. Cosmid preparations from 10 colonies showed that they all had inserts of the expected size. The 40,000 colonies were then soaked in LB medium and scraped off of the plates, then aliquoted for storage in 15% glycerol at −80° C. This represents an approximate 40-fold amplification of the *A. niger* genome.

Selection of *A. niger* prtT Clones

Cosmid DNA was prepared from the library and introduced into 13PAP2 according to the transformation procedure described by P. J. Punt and C.A.M.J.J. Van Den Hondel (1992. *Methods Enzymol* 216: 447-457). Repeated efforts to select for the pyrG marker only resulted in a recovery of between 4000 to 30,000 transformants. A double selection for the pyrG marker and growth on medium containing acetamide as the sole nitrogen source resulted in a total of 65 primary transformants from five different experiments.

Each primary transformant was screened for protease activity, growth on medium containing acetamide as the sole nitrogen source and instability of these two characteristics. An acetamidase+ phenotype, screened by growth on medium containing acetamide, is an indication of acetamidase activity resulting from activation of the pepA promoter in the reporter cassette in which the pepA promoter is linked to the amdS coding sequence. A protease+ phenotype was screened using minimal medium plates containing dialyzed skim milk as the sole nitrogen source (Mattern, I. E., et al., 1992. Mol Gen Genet. 234:332-336). On these plates the wild-type AB4.1 strain makes a clear halo whereas the AB1.13 mutant produces a very small halo. This difference is not due to differences in the activity of pepA since a pepA deleted strain can also produce a large halo on these plates. Therefore, a large halo on milk plates indicates activation of other extracellular proteases.

Instability was tested by growing diluted spore stocks on medium containing uridine. Single-spore-derived colonies were picked from these plates and tested for protease activity and growth on acetamide. The screening results revealed that in more than 70% of the colonies both characteristics were lost. Therefore, the two phenotypes were either lost or retained together, indicating that activation of the pepA promoter and other protease promoters is coordinately regulated and linked to the presence of the pyrG marker. The gene responsible for this phenotype was named prtT. Twelve acetamidase+, protease+ transformants were then isolated.

Isolation of the *A. niger* prtT Gene

In order to rescue the prtT gene from the acetamidase+, protease+ transformants of 13PAP2, DNA was prepared from mycelium grown in minimal medium as previously described. This DNA was used in an attempt to transform competent *E. coli* DH5□ cells. Several hundreds of ampicillin-resistant colonies were obtained. DNA analysis showed they all contained sequences derived from the pHelp1 plasmid. Cosmid DNA isolated from *E. coli* colonies was then retransformed into 13PAP2. Two DNA samples gave rise to transformants, which showed both growths on acetamide containing medium and increased protease activity. DNA from one of the cosmids, ACR1, was then digested with several restriction enzymes. The resulting fragments were then co-transformed with pAopyrGcosArp1 into strain 13PAP2. EcoRI, PstI, BamHI and KpnI digestion of ACR1 gave rise to transformants capable of growth on acetamide and high protease activity, whereas SalI and HindIII digests did not. Because EcoRI digestion gave the simplest pattern, separate EcoRI fragments were gel-isolated and with pAopyrGcosArp1 used to co-transform 13PAP2. Only one fragment, a 15 kb EcoRI fragment, gave rise to transformants capable of growth on acetamide-containing medium. This fragment was subcloned in pBluescript II SK in order to subclone prtT from the cosmid. Since the insert of this clone was still rather large, separate PstI bands were gel isolated and each was co-transformed with pAopyrGcosArp1 into 13PAP2. Only one band, a 2.5 kb PstI fragment, gave rise to transformants that could grow on acetamide-containing medium. This fragment was subcloned in pBlueScript II SK. Four subclones, ClE 0.7, ClE 1.8, NcE 1.1 and NcE 1.4, were constructed from this plasmid based on the restriction map. In addition, a 6.5 kb SstI/EcoRI fragment encompassing the 2.5 kb PstI fragment was subcloned, resulting in pEES1 (shown in FIG. 3).

Southern blot analysis of genomic DNA from AB4.1 showed the presence of only one copy of prtT.

Example 2

Sequencing of the *A. niger* prtT Gene and Analysis of the Sequence

All sequence reactions were prepared using dRhodamine Terminator Cycle Sequencing Kits or BigDye™ Terminator Cycle Sequencing Kits from the Perkin-Elmer Corporation (Branchburg N.J., USA). The reactions were run on an ABI PRISM® 377 DNA Sequencer (Perkin-Elmer Corporation) following the manufacturer's instructions.

The prtT gene was sequenced from the genomic clones ClE 0.7, ClE 1.8, NcE 1.1, NcE 1.4 and pEES1. The sequence specific primers used are listed below:

```
122958:
CGA TCG ATG ACT GCC TGT              (SEQ ID NO: 9)

122956:
AGA GAC ACA TAG TGC CTT              (SEQ ID NO: 10)

122959:
GCT TAT AGT CGA TAG CGC              (SEQ ID NO: 11)

122960:
CCT CTC TCC AGC GAT GGT              (SEQ ID NO: 12)

122962:
ATG GAA TAC ATA CTG CTT              (SEQ ID NO: 13)

122961:
ATG AAA CCC ACT GTA GCT              (SEQ ID NO: 14)

122963:
TGC TCG ATA AGC GGG TCC              (SEQ ID NO: 15)

122964:
AAT CTT ATG GAC CCG CTT              (SEQ ID NO: 16)

124289:
CCC CGG GAA ACA AGA ACA GG           (SEQ ID NO: 17)

124290:
GTT GGC GGA CCT TGA CTA TG           (SEQ ID NO: 18)

125112:
ACA GCT ACA GTG GGT TTC ATC T        (SEQ ID NO: 19)

125111:
AGT CAA CGG GGG AAG TCT C            (SEQ ID NO: 20)

128330:
CTA GCA GCG TAT CGG TCA GC           (SEQ ID NO: 21)

130887:
CTT GGA AAA GAA ACG ATA G            (SEQ ID NO: 22)

130888:
AAC GTA CGC TTT CCT CCT T            (SEQ ID NO: 23)

134135:
GGG TCC GTC CAG TCC GTT CTT          (SEQ ID NO: 24)

-48 reverse:
AGC GGA TAA CAA TTT CAC ACA GGA      (SEQ ID NO: 25)

-40 universal:
GTT TTC CCA GTC ACG AC               (SEQ ID NO: 26)
```

A mutant allele of the gene was obtained by PCR amplification of genomic DNA isolated from the mutant strain AB1.13 using the following primers:

```
PstI:
TC ATC CCT GGT GTT ACT GC    (SEQ ID NO: 27)

PstII:
C ATG GAT TGG CTG GCC G      (SEQ ID NO: 28)
```

The complete DNA sequence of the prtT gene is shown in SEQ ID NO: 1. The sequence of the PCR fragment of the mutant allele is shown in SEQ ID NO: 4.

Analysing the DNA sequence SEQ ID NO: 1 using the computer software Netgene 2 (S. M. Hebsgaard, P. G. Korning, N. Tolstrup, J. Engelbrecht, P. Rouze, S. Brunak (1996. Nucleic Acids Research 24: 3439-3452) suggested the existence of 5 exons (see annotations to SEQ ID NO 1).

Analysis of the *A. niger* prtT cDNA mRNA was purified from total RNA (isolated according to the DNA isolation method described above in Example 1) using a commercial poly(A)$^+$ RNA isolation kit (Pharmacia, Uppsala SE) from a culture of *A. niger* grown under conditions favourable for protease production (J.P.T.W. Van Den Hombergh, et al., 1997. Eur. J. Biochem. 247:605-613). Double stranded cDNA was prepared using standard procedures and used for PCR reactions with the following primers:

```
oligo-dT primer:
T20N

Prt270n:
TACTCTCCAGATTGCCTG           (SEQ ID NO: 29)

Prt1420r:
TGAGATACCACTCAGCAG           (SEQ ID NO: 30)

prt1350n:
TGCACTTCTCTGTCTCTG           (SEQ ID NO: 31)

Prt2365r:
GACTTCTGGCATCAGTTG           (SEQ ID NO: 32)

prt2320n:
CTCATGGATGGCATGATC           (SEQ ID NO: 33)
```

A PCR reaction with the primers Prt270n and Prt1420r produced a fragment of approximately 1.0 kb. The fragment was cloned into a pGEM-T vector (Promega Corp., Madison Wis., USA), and the insert in the resulting plasmid was sequenced using the primers 122958, 122960, −40 universal and −48 reverse. The result confirmed the presence of two introns in this part of the gene.

A second PCR reaction with the primers Prt1350n and Prt2365r produced a fragment of approximately 0.9 kb. This fragment was also cloned in a pGEM-T vector, and the insert in the resulting plasmid was sequenced using the primers 124289, 124290, −40 universal and −48 reverse. The result confirmed the presence of a single intron in this part of the gene.

Another PCR reaction with the oligo-dT primer and primer Prt2320n produced a fragment of approximately 350 bp. This fragment was also cloned in a pGEM-T vector. Sequencing of the insert using primers −40 universal and −48 reverse showed that the fragment contained the 3' part of prtT and confirmed the presence of another intron.

The deduced protein sequence of the translated prtT gene is shown in SEQ ID NO: 2. The deduced protein sequence of the translated mutant allele prt13 is shown in SEQ ID NO: 5. A comparison of SEQ ID NO: 2 and SEQ ID NO: 5 indicates that the only difference between the two is in position 112 where the leucine residue in the translated prtT gene is replaced by proline in the translated prt13 gene.

Analysis of the deduced PrtT protein sequence reveals the presence of a Zinc(II)2Cys6 binuclear cluster DNA binding motif (SEQ ID NO: 2, residues 47-81). This motif defines the GAL4 class of fungal transcriptional activators (Reece, M. J., and Ptashne, M. 1993. Science 261: 909-911). The presence of the motif in the prtT gene strongly indicates that prtT is a transcriptional activator.

Example 3

Disruption of the prtT Gene in a Wild-Type *A. niger* Strain

Figure 4:
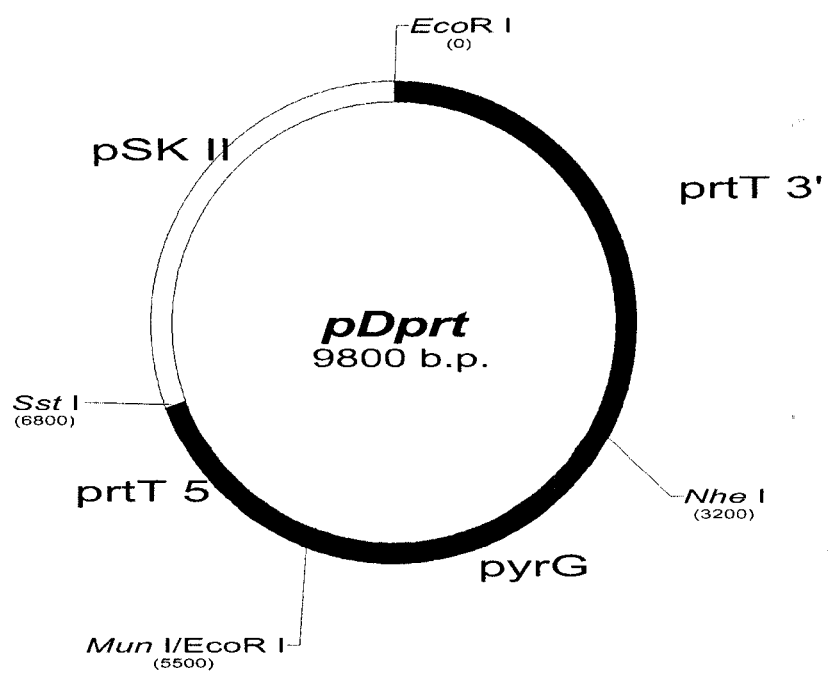
FIG. 4 shows a restriction map of the plasmid pDprt, the construction of which is described in Example 3.

A plasmid was constructed in which the upstream and downstream sequences of the prtT gene are separated by the *A. oryzae* pyrG gene. Plasmid pEES1 was digested with MunI and NheI, which removed a 2.1 kb fragment containing most of the coding sequence of prtT. A 2.3 kb EcoRI/NheI fragment from pAO4-13 containing the *A. oryzae* pyrG gene was cloned in the MunI and NheI sites of pEES1. The resulting plasmid, shown in FIG. 4, was named pDprt. This construct was then used to transform *A. niger* strain AB4.1 to uridine prototrophy. About 150 uridine prototrophic transformants were then analyzed for protease activity on skim milk containing plates. Five of these did not make a halo on these plates indicating that protease activity was very low. Comparison of strains with a disrupted prtT gene and the mutant AB1.13 strain did not show any differences in protease activity or phenotype.

Example 4

Overexpression of *A. niger* PrtT

Figure 5:
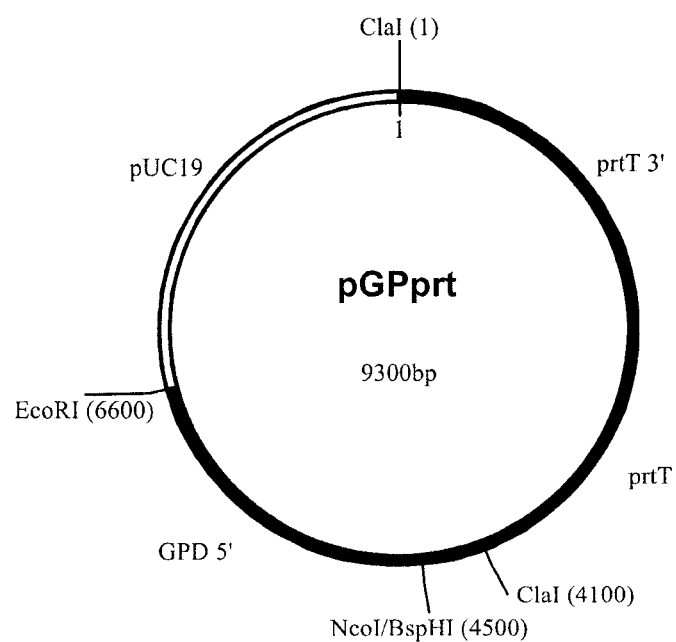
FIG. 5 shows a restriction map of the plasmid pGPprt, the construction of which is described in Example 4.

A plasmid, pGPprt, (FIG. 5) containing the coding region and 3' noncoding sequences of prtT fused to the promoter of the *A. niger* gpd gene was constructed. The gpd gene codes for glyceraldehyde-3-phosphate dehydrogenase, a constitutively expressed enzyme involved in primary metabolism. The promoter used was a fragment upstream of the coding region.

The plasmid is transformed into *A. niger* AB4.1 by cotransformation with the pyrG selection plasmid pAO4-13. Transformants with increased prtT transcription as determined by Southern blot analysis is analysed for increased protease expression.

Example 5

Isolation of the $Zn^{2+}$-Finger from the *A. oryzae* prtT Gene

The *A. niger* prtT gene is shown in SEQ ID NO: 1. The protein sequence deduced from the DNA sequence of prtT (SEQ ID NO: 2) contains a so called $Zn^{2+}$-finger motif expected to be responsible for the DNA binding of the transcriptional activator encoded by prtT. The $Zn^{2+}$-finger motif has the following amino acid sequence: Met Thr Ala Cys His Thr Cys Arg Lys Leu Lys Thr Arg Cys Asp Leu Asp Pro Arg Gly His Ala Cys Arg Arg Cys Leu Ser Leu Arg Ile Asp Cys (SEQ ID NO: 34).

Degenerate primers able to code for amino acid sequences from the motif were designed and synthesized by DNA Technology A/S, Forskerparken, Gustav Wieds vej 10, DK-8000 Aarhus C, Denmark. The primers had the following sequences:

137396:

(SEQ ID NO: 35)
A T G A C C/T G C C/T T G C/T C A C/T A C C/T T G

137397:

(SEQ ID NO: 36)
A A/G A/G C A A/G/C/T C G A/G/C/T C G A/G C A A/G G C A/G T G

The primers were used in a PCR reaction with genomic *A. oryzae* IFO4177 DNA as template. The reaction was performed in a total volume of 100 µl containing 154 pmol of primer 137396 and 10164 pmol of primer 137397. 30 PCR cycles with 56° C. as annealing temperature and 30 seconds elongation time were run. Another PCR reaction using *A. niger* genomic DNA and the primers 137394: ATGACTGC-CTGTCACACATG (SEQ ID NO: 37) and 137395: AGA-CAGCGACGGCACGCATG (SEQ ID NO: 38), which are specific for the *A. niger* prtT gene, was also run. In this reaction 10 pmol of each primers was used in a 100 µl reaction. Aliquots of the two reactions were applied to a 3% agarose gel. After electrophoresis three approximately equally intense bands could be seen in the *A. oryzae* reaction and two bands in the *A. niger* reaction. One of the bands in the *A. niger* reaction was more intense than the other and further had the expected size. One of the *A. oryzae* bands had the same size as the most intense *A. niger* band and was isolated from the gel. The fragment was cloned into the vector pCR2.1 (Invitrogen™). Plasmids from two individual colonies were sequenced. The sequences are shown in FIG. 1. The two sequences differ at the end reflecting their origin in different degenerate primers. They are identical in the middle 40 bp, which are amplified from the genomic DNA. These 40 basepairs encode a polypeptide identical to a part of the $Zn^{2+}$-finger of the *A. niger* prtT gene.

Example 6

Isolation of the N-Terminal of the *A. oryzae* prtT Gene

The inverse PCR method was used to isolate the *A. oryzae* prtT gene. The primers 144428: CACCGAGTTTTAAGCT-TGCGG (SEQ ID NO: 39) and 144429: CGATCTTGATC-CACGAGGG (SEQ ID NO: 40) were synthezised by DNA Technology A/S (Denmark). Genomic DNA was cut with a number of restriction enzymes and religated. The ligation mixtures were used as templates in PCR reactions with the primers 144428/144429. In a reaction with BamHI restricted and religated DNA as template a fragment of approximately 2.5 kb was observed after electrophoresis on an agarose gel. The fragment was labelled with $^{32}P$ by the random priming method and used as a probe against a filter containing a gridded cosmid library of genomic *A. oryzae* DNA. The construction of the library is described in WO 98/01470. The cosmid 11F8 showed a positive hybridization signal with the probe. A Southern blot containing DNA from 11F8 and genomic DNA restricted with BamHI, EcoRI, PstI or XhoI was probed with the 2.5 kb inverse PCR fragment. The size of hybridizing bands from genomic DNA were compared with those from the cosmid DNA. Apparently some rearrangement of the cosmid had occurred since only a minority of the bands from the genomic DNA had counterparts in the cosmid. Two hybridizing fragments from the cosmid, a 1.2 kb EcoRI fragment and a 1.0 kb PstI fragment, looked equal in size to hybridizing genomic fragments. The two fragments were sub-cloned from the cosmid and sequenced. Analysis of the sequence data showed that the fragments overlap. In total 1497 bp of sequence was obtained. Oligonucleotides encoding the $Zn^{2+}$-finger were not contained within the sequence. A BamHI site was found close to one end of the sequence in a region only covered by the EcoRI sub-clone, thus allowing the position of the sequenced genomic fragment relative to the $Zn^{2+}$-finger to be determined.

The primer 153468: CGGGATGAATTGTAGAGAGGC (SEQ ID NO: 41) was prepared by DNA Technology A/S (Denmark). The primer sequence is contained within the 1497 bp fragment. It is found at the end closest to the $Zn^{2+}$-finger and points in that direction. Two primers both of prtT $Zn^{2+}$-finger specific sequence and pointing either downstream (140358) or upstream (140359) were also prepared by DNA Technology A/S (Denmark). The sequence of the two primers are as follows: 140358: CGCAAGCT-TAAAACTCGGTGCGATC (SEQ ID NO: 42) and 140359: CCTCGTGGATCAAGATCGCA (SEQ ID NO: 43). Two PCR reactions, one with the primers 153468 and 140358 and one with 153468 and 140359, respectively, were performed with genomic DNA as template. The reaction with 153468 and 140359 gave a band of approximately 1.1 kb, the other reaction gave no visible bands, when analysed on an agarose gel. The 1.1 kb fragment was cloned into pCR4Blunt-TOPO (Invitrogen) and sequenced. The fragment contained part of the $Zn^{2+}$-finger and overlaps with the 1497 bp fragment. Translation of the sequence showed that the region immediately upstream of the $Zn^{2+}$-finger encodes a polypeptide with homology to the N-terminal of prtT from *A. niger*.

Example 7

Isolation of the Complete *A. oryzae* prtT Gene

The remaining parts of the gene were cloned by two consecutive rounds of inverse PCR. In the first inverse PCR reaction the genomic DNA was restricted with EcoRV and re-ligated. The PCR reaction was run with the primers 175653: GATGAAAAGAATAATCGGCGAG (SEQ ID NO: 44) and 175654: CGCGGCACACTACCCCCGTTG (SEQ ID NO: 45). The reaction resulted in the synthesis of a 1.9 kb fragment, which was cloned into the pCR4Blunt-TOPO vector and sequenced. Analysis of the sequence data showed that the fragment contains a gene with homology to the *A. niger* prtT gene and that the 3' end of the gene was missing. The second inverse PCR reaction was thus performed. The primers were B0403G08: ATCTAGCTCAAGCATTAGCGGC (SEQ ID NO: 46) and B0403G09: AATTTCGGCCCTT-TAGTGTCC (SEQ ID NO: 47). BglII restricted and re-ligated genomic DNA was used as template. A 2.4 kb fragment was obtained and cloned into the pCR4Blunt-TOPO vector and sequenced. Analysis of the sequence showed that the complete *A. oryzae* prtT gene had been obtained. The DNA sequence of the *A. oryzae* prtT gene is shown in SEQ ID NO: 48 and the deduced amino acid sequence of the encoded protein is shown in SEQ ID NO: 49.

Example 8

Disruption of the *Aspergillus oryzae* prtT Gene

The *A. oryzae* prtT gene was disrupted using a method of positive/negative selection. A disruption cassette consisting of 2 kb of the *A. oryzae* prtT gene (SEQ ID NO: 48) with an insertion of the pyrG gene in the middle is cloned into a vector (pDV8) containing the herpes simplex virus I tymidine kinase gene (HSV-tk) flanked by fungal expression signals. Expression of the tymidine kinase gene makes the host sensitive to 5-fluoro-2-deoxyuridine. A disrupted strain can be isolated by positive selection for the pyrG gene in a pyrG minus host and deselection of the tymidine kinase gene on 5-fluoro-2-deoxyuridine. Since the tymidine kinase gene and the pyrG gene are present in the same DNA fragment selection is for transformants in which a double cross-over event has happened. The system gives fewer transformants pr. Micro g of DNA than transformation with just a disruption cassette, but the frequency of transformants in which the desired homologous recombination event has occurred is much higher.

The pyrG gene used here is flanked by repeats enabling a later removal by selection for 5-fluoroorotic acid resistance. The pyrG gene is isolated from the plasmid pJaL554.

The pDV8 Plasmid pDV8 was kindly provided by Matthew S. Sachs, University of Oregon, PO Box 91000, Portland, Oreg. 97291-1000, USA. pDV8 (FIG. 7) is a pSP65 (Promega™) based plasmid containing the HSV-tk gene on a 1.2 kb BglII/BamHI fragment inserted between a 1.0 kb XhoI/BglII fragment of the *A. nidulans* gpd promoter and a 0.8 kb BamHI/HindIII fragment containing the *A. nidulans* trpc transcriptional terminator.

The *A. nidulans* gpd promoter and the trpc transcriptional terminator are taken from the plasmid pAN51-2 (Punt et al., (1990), Gene 93, p. 101-109). The HSV-tk gene is described by McKnight S. L., (1980), Nucleic Acids Res. 8:5949-5964, Database accession no. EMBL v00470, position 252-1479. The construction of pDV8 is described in Vaught-Alexander D (thesis) Expression of the herpes simplex virus type-1 thymidine kinase gene in *Neurospora crassa*, (1994), Oregon Graduate Institute of Science & Technology, University of Portland, PO Box 91000, Portland, Oreg. 97291-1000, USA. The sequence of pDV8 is included in this application as SEQ ID NO: 50. Single-, double- and multicopy *A. oryzae* transformants of pDV8 were isolated by transforming a pDV8 derivative containing the *A. oryzae* niaD gene into an *A. oryzae* niaD mutant. The copy number of the HSV-tk gene was determined by Southern analysis. The transformants and the untransformed host were inoculated onto plates containing varying concentrations of 5-fluoro-2'-deoxyuridine. From inspection of the growth on the plates it was decided to use 6 microM of 5-fluoro-2'-deoxyuridine in the plates for future positive/negative selection experiments. At this concentration none of the pDV8 transformants grew, while the untransformed host was only slightly inhibited.

Description of pJaL554

PJaL554 was constructed by ligating the 316 bp Asp718-NheI fragment to the 5336 bp SpeI-SspBI fragment from the pyrG containing plasmid pSO₂ (described in WO 97/35956). Thus, pJaL554 harbours the *A. oryzae* pyrG gene flanked by 316 bp repeats. The construction is illustrated in FIG. 8.

Construction of a prtT Disruption Plasmid in the pDV8 Vector

A PCR reaction is performed on chromosomal *A. oryzae* IFO4177 DNA with the primers B1042E05 and B1450E07.

B1042E05:
CGCGCGTATCCTATTGCC        (SEQ ID NO: 51)

B1450E07:
GCCGGAAATGTTGTACCTAC.     (SEQ ID NO: 52)

A fragment of 2078 basepairs is obtained and cloned into the pCR4Blunt-TOPO (Invitrogen™) vector. The resulting plasmid is sequenced with the standard M13 forward (−40) and reverse primers to ensure that the correct fragment is obtained. The PCR fragment is excised from the vector by the restriction enzyme EcoRV which cuts twice internally in the fragment. The cut sites are located at positions 1 and 1964 in SEQ ID NO: 48. The 1964 bp fragment is ligated with the pDV8 vector, which has been cut with HindIII and blunt ended by filling in the ends with the Klenow fragment of DNA polymerase I from *E. coli* and dNTP. The resulting plasmid is cut with HindIII, which is located in the prtT fragment (in the part encoding the $Zn^{2+}$-finger) at position 962 in SEQ ID NO: 48, dephosphorylated and ligated with the pyrG gene isolated from pJaL554 as a 2.5 kb HindIII fragment.

Selection of prtT Disrupted Strains

The disruption plasmid described above was linearized with NotI and transformed into *A. oryzae* HowB101 (described in WO 97/35956), a pyrG minus derivative of IFO4177. The transformation is done essential as described in EP 0 238 023. Transformants are selected on plates containing Coves salt solution (Cove DJ, (1966), Biochim. Biophys. Acta 113:51-56), 1 M sucrose for osmotic stabilization and as carbon source, 20 g/L agar, 10 mM $NaNO_3$ and 6 microM 5-fluoro-2-deoxyuridine (Sigma). The transformants are reisolated once on the same type of plates. Transformants carrying a disrupted prtT gene are identified by Southern blot analysis.

A strain carrying the prtT disruption is used as host for expression of a truncated PDI gene (Protein Disulfide isomerase gene) harbored on the expression plasmid pCaHj445 (described in U.S. Pat. No. 5,879,664). pCaHj445 is transformed into the *A. oryzae* prtT disrupted strain by cotransformation with the plasmid p3SR2 containing the *A. nidulans* amdS gene. Transformation and selection on acetamide plates is done essentially as described in EP 0 238 023. After reisolation the transformants are fermented in shake flasks or fermentors and the PDI protein is purified from the fermentation broth.

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

Various references are cited herein, the disclosures of which are incorporated by reference in their entireties.

What is claimed is:

1. A host cell for the production of a desired polypeptide, wherein the host cell comprises:

(a) a first nucleic acid sequence that encodes a polypeptide having an amino acid sequence having at least 90% sequence identity with the amino acid sequence of SEQ ID NO:49, wherein the nucleic acid sequence is altered such that the host cell produces less protease compared to a similar cell with a nucleic acid sequence that encodes a polypeptide having an amino acid sequence of SEQ ID NO:49 when cultured under the same conditions, and (b) an inducible promoter operably linked to the nucleic acid sequence, and a promoter sequence that binds a transcriptional activator encoded by the nucleic acid sequence, operably linked to a nucleic acid sequence encoding the desired polypeptide, wherein the inducible promoter and promoter sequence can be induced simultaneously or sequentially.

2. A host cell in accordance with claim 1, wherein the first nucleic acid sequence encodes polypeptide that has transcriptional activation activity.

3. A host cell in accordance with claim 1, wherein the first amino acid sequence is least 96% identical with the amino acid sequence of SEQ ID NO:49.

4. A host cell in accordance with claim 1, wherein the first amino acid sequence is least 97% identical with the amino acid sequence of SEQ ID NO:49.

5. A host cell in accordance with claim 1, wherein the first amino acid sequence is least 99% identical with the amino acid sequence of SEQ ID NO:49.

6. A host cell in accordance with claim 1, wherein the first amino acid sequence comprises the amino acid sequence of SEQ ID NO:49.

7. A host cell in accordance with claim 1, wherein the first amino acid sequence consists of the amino acid sequence of SEQ ID NO:49.

8. A host cell in accordance with claim 1, wherein the first nucleic acid sequence comprises nucleotides 977-3116 of SEQ ID NO: 48 or the cDNA thereof.

9. A host cell in accordance with claim 1, wherein the first nucleic acid sequence is obtained from an *Aspergillus* cell.

10. A host cell in accordance with claim 1, wherein the first nucleic acid sequence is obtained from an *Aspergillus, Fusarium, Penicillium* or *Trichoderma* cell.

11. The host cell of claim 1, wherein the inducible promoter is mediated by a carbon or nitrogen catabolite.

12. The host cell of claim 1, wherein the promoter sequence that binds the transcriptional activator is from a protease gene.

13. A method of producing a desired polypeptide, comprising:
   (a) cultivating the host cell of claim 1, wherein the host cell harbors a gene encoding the desired polypeptide, in a nutrient medium suitable for production of the desired polypeptide; and
   (b) recovering the desired polypeptide from the nutrient medium of the mutant cell.

14. A method of producing a desired polypeptide, comprising:
   (a) cultivating the host cell of claim 1, wherein the host cell harbors a gene encoding the desired polypeptide, in a nutrient medium suitable for production of the desired polypeptide.

15. The method of claim 14, wherein the amino acid sequence is least 99% identical with the amino acid sequence of SEQ ID NO:49.

16. The method of claim 14, wherein the amino acid sequence consists of the amino acid sequence of SEQ ID NO:49.

17. A host cell for the production of a desired polypeptide, wherein the host cell comprises:
   (a) a first nucleic acid sequence encoding a polypeptide having an amino acid sequence having at least 90% sequence identity with the amino acid sequence of SEQ ID NO:49, wherein the nucleic acid sequence is altered or inactivated such that the cell produces a reduced amount of protease, and
   (b) an inducible promoter operably linked to the nucleic acid sequence, and a promoter sequence that binds a transcriptional activator encoded by the nucleic acid sequence, operably linked to a nucleic acid sequence encoding the desired polypeptide, wherein the inducible promoter and promoter sequence can be induced simultaneously or sequentially.

* * * * *

Disclaimer

8,426,164 B2 — Carsten M. Hjort, Smorum (DK); Cees A. M. J. J. Van den Hondel, PZ Gouda (NL); Peter J. Punt, XT Houten (NL); Frank H. J. Schuren, ZK Veenendaal (NL); Tove Christensen, Lyngby (DK). FUNGAL TRANSCRIPTIONAL ACTIVATOR USEFUL IN METHODS FOR PRODUCING POLYPEPTIDES. Patent dated April 23, 2013. Disclaimer filed December 7, 2015, by the assignee, Novozymes A/S.

Hereby disclaim all complete claims 1-17 of said patent.

*(Official Gazette, April 24, 2018)*